United States Patent [19]

Xu et al.

[11] Patent Number: 6,001,825
[45] Date of Patent: *Dec. 14, 1999

[54] USE OF NOVEL ORGANOSELENIUM COMPOUNDS AS PRO-OXIDIZING AGENTS THEIR METHODS OF PREPARATION AND PHARMACEUTICAL COMPOSITIONS AND APPLICATION THEREOF

[75] Inventors: Jinzhu Xu, Ivry sur Seine; Georges Appere, Sucy en Brief; Jean Chaudiere, Saint Maur; Jean-Claude Yadan, Paris, all of France

[73] Assignee: Oxis Isle of Man, Limited, Portland, Oreg.

[*] Notice: This patent issued on a continued prosecution application filed under 37 CFR 1.53(d), and is subject to the twenty year patent term provisions of 35 U.S.C. 154(a)(2).

[21] Appl. No.: 08/771,442

[22] Filed: Dec. 20, 1996

[30] Foreign Application Priority Data

Jul. 17, 1996 [FR] France ..................................... 96 08929

[51] Int. Cl.$^6$ ........................ A61K 33/04; C07D 293/12; C07D 293/10; C07J 51/00
[52] U.S. Cl. ......................... 514/176; 514/359; 540/107; 540/108; 540/117; 548/121
[58] Field of Search ............................ 548/121; 514/359, 514/176; 540/108, 107, 117

[56] References Cited

FOREIGN PATENT DOCUMENTS 3027074   2/1982   Germany .
WO 95/27706  10/1995   WIPO .

OTHER PUBLICATIONS

Emerit, I. (1994) Free Radic. Bio. Med. 16:99–109.
Blasig et al. (1994) Free Radic. Biol. Med. 16:35–41.
Walton et al. (1992) Int. J. Radiat. Oncol. Biol. Phys. 22:643–7.
Chaudiere et al. (1992) Arch. Biochem. Biophys. 296:328–36.
Said et al. (1989) Ann. Rev. Resp. Dis. 139:1553–64.
Sinha et al. (1987) Biochem. 26:3776–81.
Smith, L.L. (1986) Ann. Rev. Physiol. 48:681–92.
Doroshow, J.H. (1986) P.N.A.S. 83:4514–8.
Troll et al. (1985) Ann. Rev. Pharmocol. Toxicol. 25:509–28.
Ames, B.N. (1983) Science 221:1256–64.
Umezama, H. (1979) In: Bleomycin: chemical, biochemical and biological apsects. Hecht, S.M. ed., Spring Verlag, NY, pp. 24–36.
Dische et al. (1979) Int. J. Radiat. Oncol. Biol. Phys. 5:851–60.
Christian Lambert et al. (1991) Tetrahedron. 47:9053–60.

Primary Examiner—Mukund J. Shah
Assistant Examiner—Bruck Kifle
Attorney, Agent, or Firm—Klauber & Jackson

[57] ABSTRACT

Compounds represented by the following formula I:

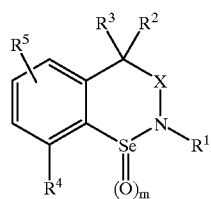

in which:

$R^1$ to $R^5$ can have various meanings of which alkyl, substituted or non-substituted aryl, and m is equal to 0 or 1, X is selected from $(CR^6R^7)_n$ in which n=0 or 1, and CO are disclosed. These compounds are useful as anti-tumor drugs, especially with pro-oxidizing activity.

12 Claims, 9 Drawing Sheets

Map of reference field/frame with odd number of macroblocks in a line
FIG. 4A
FIG. 4B
Map of reference field/frame with even number of macroblocks in a line
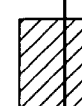
FIG. 4C
FIG. 4D

| Page Read Order | Page Misses |
|---|---|
| y0: ABC* | 3 (ABC) |
| y1: CA | +1 (A) |
| y2: ABC* | +2 (BC) |
| y3: CA | +1 (A) |
| *No page misses | 7 Total |

USE OF NOVEL ORGANOSELENIUM COMPOUNDS AS PRO-OXIDIZING AGENTS THEIR METHODS OF PREPARATION AND PHARMACEUTICAL COMPOSITIONS AND APPLICATION THEREOF

The present invention relates to the use of novel organoselenium compounds as pro-oxidizing agents, their methods of preparation and pharmaceutical compositions and application thereof.

PRIOR ART

The reactive oxygen entities (ROEs), such as, for example, the superoxide anion ($O_2$) and hydrogen peroxide ($H_2O_2$), coming from metabolism of oxygen, generated within the cell are under the control of the antioxidizing protection system. This system is composed in particular of macromolecules with enzymatic activity such as superoxide dismutases (SOD), catalase and glutathione peroxidases, as well as small molecules with high reducing potential such as, for example, glutathione, vitamin E, vitamin C and lipoic acid. This antioxidizing system plays a central role in the prevention of <<oxidative stress>> and its deleterious consequences (1).

In normal physiological situations, an equilibrium between the production and the decomposition of these reactive oxygen entities (ROEs) already exists in the cell. If this fragile equilibrium becomes durably disrupted under the influence of a physical stimulus (UV, ionizing radiation, . . . ), or an internal chemical stimulus (cytokines), or an external chemical stimulus (xenobiotics, cigarettes, . . . ) the production of these ROEs surpassing the antioxidizing protection system, the cellular structures (membranes, mitochondria, DNA, . . . ) are destroyed. This phenomenon being able to lead irreversibly to cellular death if this imbalance attains a critical threshold. This general physiopathological mechanism has been proposed in a large number of diseases such as inflammatory diseases (see Ann. Rev. Physiol.; 1986, 48, 681–692 and Ann. Rev. Resp. Dis. 1989, 139, 1553–1564), cardiovascular diseases (see Free Radic. Biol. Med.; 1994, 16, 35–41), the genesis of certain cancers (see Science; 1983, 221, 1256–1264 and Ann. Rev. Pharmacol. Toxicol.; 1985, 25, 509–528 as well as Free Radic. Biol. Med.; 1994, 16, 99–109) as well as for the phenomenon of ageing.

The controlled generation of these ROEs has proved to be formidable weapon for the destruction of certain target cells such as tumor cells. The pharmocological concept consisting in the use of cytotoxic drugs which generate reactive oxygen entities was implicitly bound to the mode of action of anti-cancer drugs such as, for example, bleomycin (see <<Bleomycin: chemical, biochemical and biological aspects>>; Hecht S. M. ed.; (1979); Springer Verlag, N.Y.; 24) whose target is DNA, anthracyclines (daunorubicin, daunomycin, . . . ) (see P. N. A. S.; 1986, 83, 4514 and Biochem.; 1987, 26, 3776), mitomycin C and its analogues Int. J. Radiat. Oncol. Biol. Phys.; 1979, 5, 851), nitroimidazoles (misonidazole, pimonidazole, . . . ) (see Int. J. Radiat. Oncol. Biol. Phys.; 1992, 22, 643 and 649) amongst others.

Furthermore, it has been demonstrated that the toxicity of organoselenium compounds of the selenol and/or diselenide type is in a large part due to the catalytic reduction of oxygen giving superoxide and hydrogen peroxide (see Arch. Biochem. Biophys.; 1992, 296, 328–336).

On the other hand, various benzisoselenazolines and benzisoselenazines were described by the Applicant in the prior patent application Ser. No. 2 718 441 which possess a therapeutic activity as antioxidizing and anti-inflammatory agents. The substituents on the benzene ring can occupy any of the positions and no compound described possesses an aromatic substituent in a position ortho to the selenium, with the exception of one sole compound which possesses a nitro substitution in ortho combined with a dimethyl substitution in benzylic position.

One of the aims of the present invention is to conceive organoselenium compounds possessing a catalytic pro-oxidizing activity, i.e. an activity generating reactive oxygen entities which can destroy a target cell, in particular a pathogenic cell, such as a tumor cell.

These compounds must be able to penetrate the interior of the target tissues or cells, they must be water-soluble at active concentrations and must efficiently reduce oxygen to give toxic by-products.

These aims are attained by this invention which consists in the design of novel organoselenium derivatives whose pro-oxidizing and cytotoxic activities as well as their methods of preparation are described.

It is completely surprising, in the framework of the present invention, that the organoselenium derivatives possess a pro-oxidizing activity, given that the organoselenium compounds described in the prior application of the applicant, FR-A-94 04107, which had been shown to possess an anti-oxidizing activity and had been tested as such. From this fact, although it had been described that the radicals $R^1$ and $R^2$ could stand for —$NO_2$, in general, their position on the benzene ring was not specified and only one example described the synthesis of a derivative bearing a nitro group in the position ortho to the selenium on the benzene ring. This compound was claimed as a novel compound, but was inactive as an anti-oxidizing agent.

DESCRIPTION OF THE INVENTION

The aim of the present invention is:
1) to solve the novel technical problem consisting in providing novel organoselenium derivatives possessing excellent pro-oxidizing and cytotoxic activities, which can thus constitute a valuable active ingredient in the framework of pharmaceutical compositions;
2) to solve the novel technical problem, set forth above, with a solution which also provides a method for the preparation of these compounds which is relatively easy to carry out;

These aspects of the technical problem described above are simultaneously solved by the present invention by a simple solution, with a preparation method which is relatively easy to carry out and which gives good yields.

In a first aspect, the present invention provides novel organoselenium compounds of the following general formula(I):

General Formula I

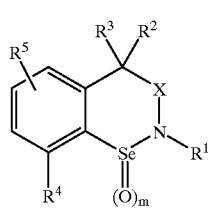

wherein:

$R^1$ is selected from a group consisting of: hydrogen; $C_1$–$C_6$ alkyl; ar($C_1$–$C_6$)alkyl; ar($C_1$–$C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo ($C_1-C_6$-alkyl), —$CO_2H$, and —$CO_2$—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; —$COR^8$; —$COOR^8$; —$CONH_2$; —$CONR^8R^9$; —$(CH_2)_pR^{10}$; and —$(CH_2)_p$Vect;

$R^2$ is selected from the group consisting of: hydrogen; $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; —$COR^8$; —$COOR^8$; —$CONH_2$; —$CONR^8R^9$; —$(CH_2)_pR^{10}$; and —$(CH_2)_p$Vect;

$R^3$ is selected from the group consisting of: hydrogen; $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; —$COR^8$; —$COOR^8$; —$CONH_2$; —$CONR^8R^9$; —$(CH_2)_pR^{10}$; and —$(CH_2)_p$Vect;

$R^4$ is selected from the group consisting of: —$NO_2$; —NO; —CN; —$COOR^9$; —$SO_3R^9$; —$CONR^9R^{11}$ and —$SO_2NR^9R^{11}$;

$R^5$ is selected from the group consisting of: hydrogen; $C_1-C_6$ alkyl; —$COR^8$; —$COOR^8$; —$CONR^8R^9$; —$(CH_2)_pR^{10}$; —$(CH_2)_p$Vect; —$N^+R^{11}_3Y^-$; —$SO_3^-Z^+$ and —$CO_2^-Z^+$;

X is selected from the group consisting of: $(CR^6R^7)_n$; and CO;

$R^6$ is selected from the group consisting of: hydrogen; $C_1-C_6$ alkyl; —$COR^8$; —$COOR^8$; —$CONR^8R^9$; —$(CH_2)_pR^{10}$; and —$(CH_2)_p$Vect;

$R^7$ is selected from the group consisting of: hydrogen; $C_1-C_6$ alkyl; —$COR^8$; —$COOR^8$; —$CONR^8R^9$; —$(CH_2)_pR^{10}$; and —$(CH_2)_p$Vect;

$R^8$ is selected from the group consisting of: $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl) amino, sulfonyl, sulfonamide, sulfo($C_1-C_6$-alkyl), —$CO_2H$, and —$CO_2$—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo ($C_1-C_6$-alkyl), —$CO_2H$, and —$CO_2$—($C_1-C_6$)alkyl; heteroaryl; heteroaryl substituted by one or more identical or different groups selected from: $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; and —$(CH_2)_p$Vect;

$R^9$ is selected from the group consisting of: hydrogen; $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; and —$(CH_2)_p$Vect;

$R^{10}$ is selected from the group consisting of: hydrogen; —$N^+R^{11}_3Y^-$; —$SO_3^-Z^+$ and —$CO_2^-Z^+$;

$R^{11}$ is selected from the group consisting of: hydrogen; $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —$CO_2H$, and —$CO_2$—($C_1-C_6$)alkyl;

Vect=

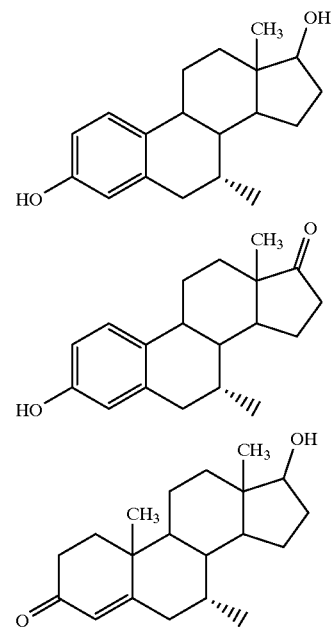

-continued

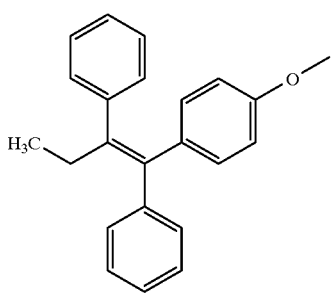

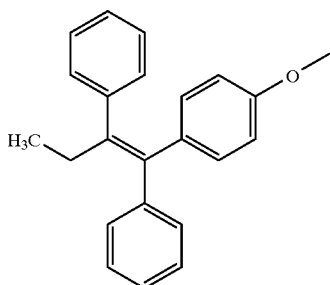

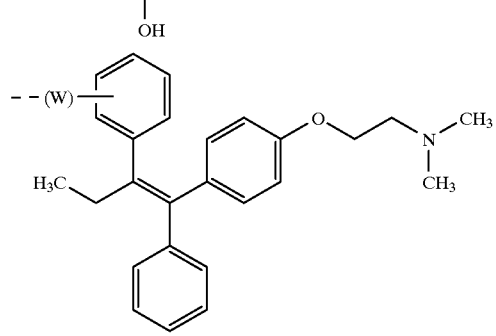

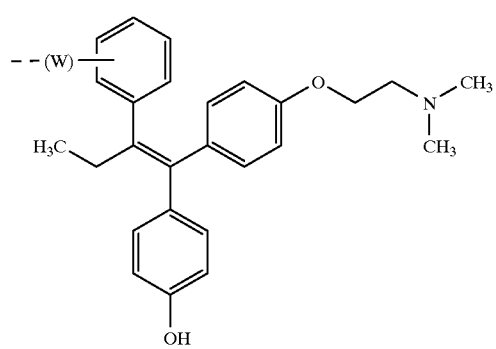

W represents either a simple linkage with $-(CH_2)_p-$, or a heteroatom such as O, S or N, bound to $-(CH_2)_p-$;

$Y^-$ represents the anion of a pharmaceutically acceptable acid;

$Z^+$ represents the cation of a pharmaceutically acceptable base;

n=0, 1;
m=0, 1;
p=2 to 10;

and their salts of pharmaceutically acceptable acids or bases;

with the proviso that there can not be more than one Vect substituent within each molecule of the general formula I.

With the further proviso that:

When $R^4$ is $-NO_2$, then at least one of $R^2$ and $R^3$ is other than methyl.

In the framework of the description and the claims:

the term <<lower alkyl group>> or <<$C_1-C_6$ alkyl group>> means linear or branched groups containing 1 to 6 carbon atoms;

the term <<substituted>>, as applied to the aryl or aralkyl groups, means that these are substituted in the aromatic portion by one or more identical or different groups selected from: $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo ($C_1-C_6$-alkyl), $-CO_2H$; $-CO_2-(C_1-C_6)$alkyl; or by one or more hydrogen atoms;

when $R^4$ represents $-COOH$, $-SO_3H$, the invention also covers the addition salts of a pharmaceutically acceptable base.

Amongst the pharmaceutically acceptable acids, cited in a non-limiting way, are: hydrochloric, hydrobromic, hydroiodic, sulfuric, tartaric, methanesulfonic, trifluoromethanesulfonic acid, etc. . . .

Amongst the pharmaceutically acceptable bases, cited in a non-limiting way, are: sodium and potassium hydroxides, alkali metal or alkaline-earth metal carbonates or organic bases such as triethylamine or arginine, etc. . .

In a second aspect, the present invention relates to the use of organoselenium compounds of the following general formula (IA):

General Formula IA

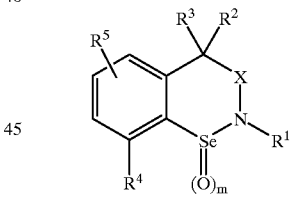

wherein:

$R^1$ is selected from a group consisting of: hydrogen; $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), $-CO_2H$, and $-CO_2-(C_1-C_6)$alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), $-CO_2H$, and $-CO_2-(C_1-C_6)$alkyl; $-COR^8$; $-COOR^8$; $-CONH_2$; $-CONR^8R^9$; $-(CH_2)_pR^{10}$; and $-(CH_2)_p$ Vect;

$R^2$ is selected from the group consisting of: hydrogen; $C_1-C_6$ alkyl; ar($C_1-C_6$)alkyl; ar($C_1-C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; —$COR^8$; —$COOR^8$; —$CONH_2$; —$CONR^8R^9$; —$(CH_2)_pR^{10}$; and —$(CH_2)_p$Vect;

$R^3$ is selected from the group consisting of: hydrogen; $C_1$–$C_6$ alkyl; ar($C_1$–$C_6$)alkyl; ar($C_1$–$C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; —$COR^8$; —$COOR^8$; —$CONH_2$; —$CONR^8R^9$; —$(CH_2)_pR^{10}$; and —$(CH_2)_p$Vect;

$R^4$ is selected from the group consisting of: —$NO_2$; —NO; —CN; —$COOR^9$; —$SO_3R^9$; —$CONR^9R^{11}$ and —$SO_2NR^9R^{11}$;

$R^5$ is selected from the group consisting of: hydrogen; $C_1$–$C_6$ alkyl; —$COR^8$; —$COOR^8$; —$CONR^8R^9$; —$(CH_2)_pR^{10}$; —$(CH_2)_p$Vect; —$N^+R^{11}_3Y^-$; —$SO_3^-Z^+$ and —$CO_2^-Z^+$;

X is selected from the group consisting of: $(CR^6R^7)_n$; and CO;

$R^6$ is selected from the group consisting of: hydrogen; $C_1$–$C_6$ alkyl; —$COR^8$; —$COOR^8$; —$CONR^8R^9$; —$(CH_2)_pR^{10}$; and —$(CH_2)_p$Vect;

$R^7$ is selected from the group consisting of: hydrogen; $C_1$–$C_6$ alkyl; —$COR^8$; —$COOR^8$; —$CONR^8R^9$; —$(CH_2)_pR^{10}$; and —$(CH_2)_p$Vect;

$R^8$ is selected from the group consisting of: $C_1$–$C_6$ alkyl; ar($C_1$–$C_6$)alkyl; ar($C_1$–$C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl) amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo ($C_1$–$C_6$-alkyl), —$CO_2H$, and —$CO_2$—($C_1$–$C_6$)alkyl; heteroaryl; heteroaryl substituted by one or more identical or different groups selected from: $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; and —$(CH_2)_p$Vect;

$R^9$ is selected from the group consisting of: hydrogen; $C_1$–$C_6$ alkyl; ar($C_1$–$C_6$)alkyl; ar($C_1$–$C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; and —$(CH_2)_p$Vect;

$R^{10}$ is selected from the group consisting of: hydrogen; —$N^+R^{11}_3Y^-$; —$SO_3^-Z^+$ and —$CO_2^-Z^+$;

$R^{11}$ is selected from the group consisting of: hydrogen; $C_1$–$C_6$ alkyl; ar($C_1$–$C_6$)alkyl; ar($C_1$–$C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl;

Vect=

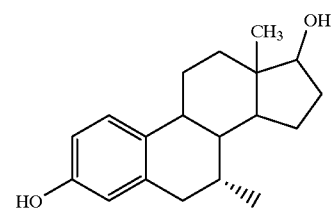

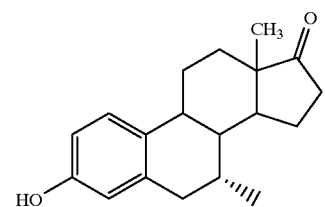

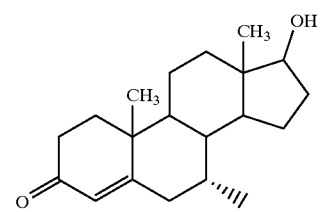

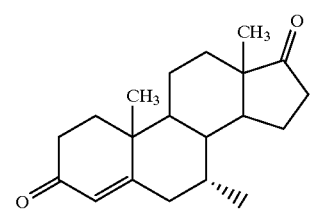

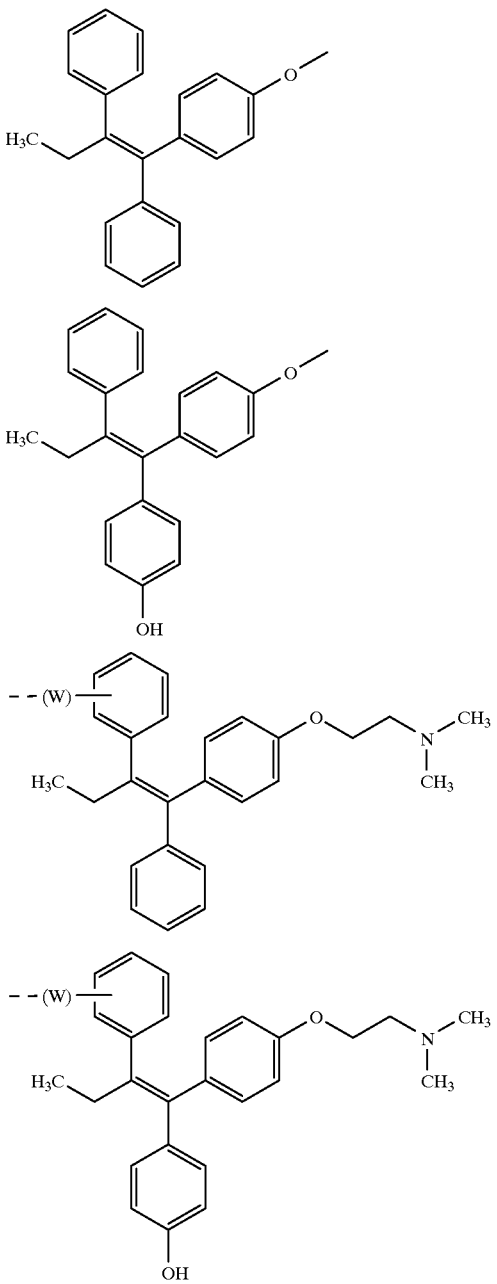

W represents either a simple linkage with —(CH$_2$)$_p$—, or a heteroatom such as O, S or N, bound to —(CH$_2$)$_p$—;

Y$^-$ represents the anion of a pharmaceutically acceptable acid;

Z$^+$ represents the cation of a pharmaceutically acceptable base;

n=0, 1;

m=0, 1;

p=2 to 10;

and their salts of pharmaceutically acceptable acids or bases;

with the proviso that there can not be more than one Vect substituent within each molecule of the general formula IA;

as a pro-oxidizing agent.

The invention also covers the methods of therapeutic treatment corresponding to this use, as is well understandable for a person skilled in the art.

In an advantageous embodiment, the present invention relates to the use of the above-mentioned compounds of general formula IA for the manufacture of a pharmaceutical composition with pro-oxidizing activity, in particular in the treatment of cancers in which an intracellular overproduction of cytotoxic reactive oxygen entities contributes to functional alterations in the corresponding tumor cells.

In these cancerous pathologies, the active ingredient can be administered via the oral, rectal or topical route, or even by intramuscular or intravenous injection.

In another advantageous embodiment, the organoselenium derivative of the above-mentioned general formula (IA) is present in an amount in the range 0.01% to 5% by weight with respect to the total weight of the final composition, preferably in the range 0.1% to 1% by weight.

In another advantageous embodiment, the present invention relates to the use of the composition in the form of unit dose which may comprise 1 mg to 500 mg of the organoselenium derivative of the above-mentioned general formula (IA), optionally in a pharmaceutically acceptable excipient, vehicle or support.

In a third aspect, the present invention also provides a pharmaceutical composition, in particular with pro-oxidizing activity, characterized in that it comprises, as active ingredient, at least one organoselenium derivative of the following general formula (IA):

General Formula IA

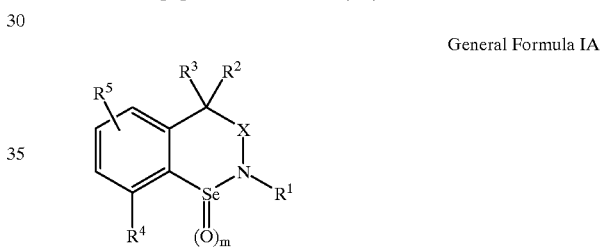

wherein:

R$^1$ is selected from a group consisting of: hydrogen; C$_1$–C$_6$ alkyl; ar(C$_1$–C$_6$)alkyl; ar(C$_1$–C$_6$)alkyl substituted on aryl by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; aryl; aryl sustituted by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; —COR$^8$; —COOR$^8$; —CONH$_2$; —CONR$^8$R$^9$; —(CH$_2$)$_p$R$^{10}$; and —(CH$_2$)$_p$Vect;

R$^2$ is selected from the group consisting of: hydrogen; C$_1$–C$_6$ alkyl; ar(C$_1$–C$_6$)alkyl; ar(C$_1$–C$_6$)alkyl substituted on aryl by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; aryl; aryl sustituted by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; —COR$^8$; —COOR$^8$; —CONH$_2$; —CONR$^8$R$^9$; —(CH$_2$)$_p$R$^{10}$; and —(CH$_2$)$_p$Vect;

R$^3$ is selected from the group consisting of: hydrogen; C$_1$–C$_6$ alkyl; ar(C$_1$–C$_6$)alkyl; ar(C$_1$–C$_6$)alkyl substituted on aryl by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; aryl; aryl sustituted by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; —COR$^8$; —COOR$^8$; —CONH$_2$; —CONR$^8$R$^9$; —(CH$_2$)$_p$R$^{10}$; and —(CH$_2$)$_p$Vect;

R$^4$ is selected from the group consisting of: —NO$_2$; —NO; —CN; —COOR$^9$; —SO$_3$R$^9$; —CONR$^9$R$^{11}$ and —SO$_2$NR$^9$R$^{11}$;

R$^5$ is selected from the group consisting of: hydrogen; C$_1$–C$_6$ alkyl; —COR$^8$; —COOR$^8$; —CONR$^8$R$^9$; —(CH$_2$)$_p$R$^{10}$; —(CH$_2$)$_p$Vect; —N$^+$R$^{11}$$_3$Y$^-$; —SO$_3$$^-$Z$^+$ and —CO$_2$$^-$Z$^+$;

X is selected from the group consisting of: (CR$^6$R$^7$)$_n$; and CO;

R$^6$ is selected from the group consisting of: hydrogen; C$_1$–C$_6$ alkyl; —COR$^8$; —COOR$^8$; —CONR$^8$R$^9$; —(CH$_2$)$_p$R$^{10}$; and —(CH$_2$)$_p$Vect;

R$^7$ is selected from the group consisting of: hydrogen; C$_1$–C$_6$ alkyl; —COR$^8$; —COOR$^8$; —CONR$^8$R$^9$; —(CH$_2$)$_p$R$^{10}$; and —(CH$_2$)$_p$Vect;

R$^8$ is selected from the group consisting of: C$_1$–C$_6$ alkyl; ar(C$_1$–C$_6$)alkyl; ar(C$_1$–C$_6$)alkyl substituted on aryl by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; aryl; aryl sustituted by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; heteroaryl; heteroaryl substituted by one or more identical or different groups selected from: C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; and —(CH$_2$)$_p$Vect;

R$^9$ is selected from the group consisting of: hydrogen; C$_1$–C$_6$ alkyl; ar(C$_1$–C$_6$)alkyl; ar(C$_1$–C$_6$)alkyl substituted on aryl by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; aryl; aryl sustituted by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; and —(CH$_2$)$_p$Vect;

R$^{10}$ is selected from the group consisting of: hydrogen; —N$^+$R$^{11}$$_3$Y$^-$; —SO$_3$$^-$Z$^+$ and —CO$_2$$^-$Z$^+$;

R$^{11}$ is selected from the group consisting of: hydrogen; C$_1$–C$_6$ alkyl; ar(C$_1$–C$_6$)alkyl; ar(C$_1$–C$_6$)alkyl substituted on aryl by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl; aryl; aryl sustituted by one or more identical or different groups selected from C$_1$–C$_6$ alkyl, trifluoromethyl, C$_1$–C$_6$ alkoxy, hydroxyl, nitro, amino, C$_1$–C$_6$ alkylamino, di(C$_1$–C$_6$-alkyl)amino, sulfonyl, sulfonamide, sulfo(C$_1$–C$_6$-alkyl), —CO$_2$H, and —CO$_2$—(C$_1$–C$_6$)alkyl;

Vect=

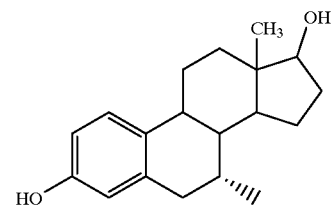

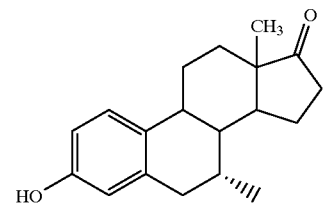

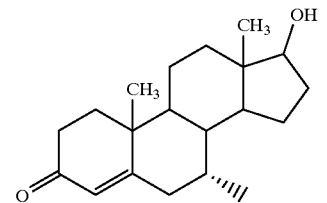

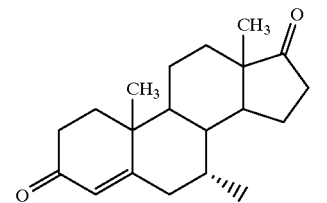

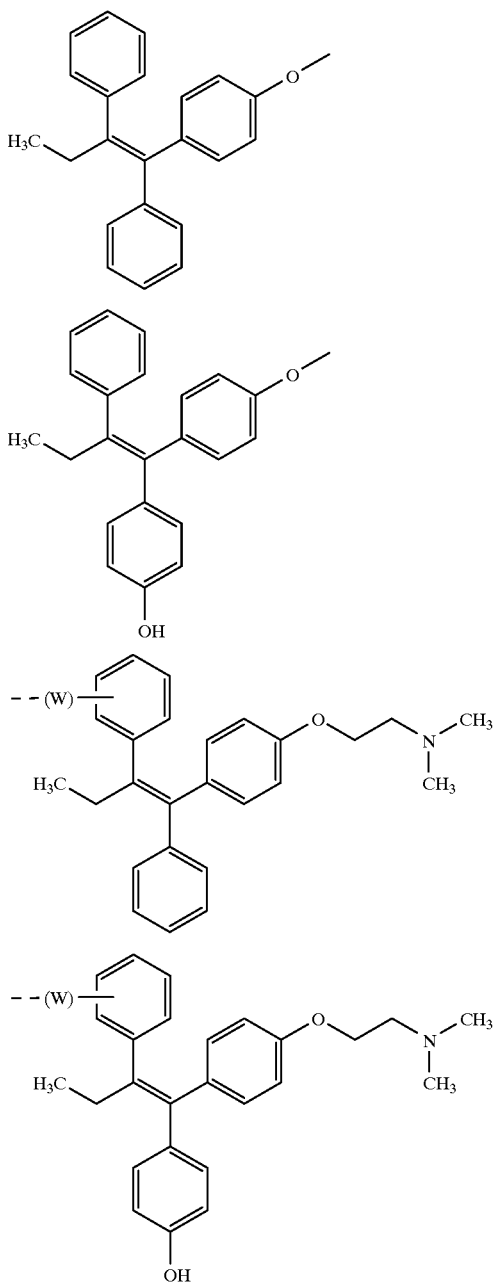

W represents either a simple linkage with —(CH$_2$)$_p$—, or a heteroatom such as O, S or N, bound to —(CH$_2$)$_p$—;

Y$^-$ represents the anion of a pharmaceutically acceptable acid;

Z$^+$ represents the cation of a pharmaceutically acceptable base;

n=0, 1;
m=0, 1;
p=2 to 10;

and their salts of pharmaceutically acceptable acids or bases;
with the proviso that there can not be more than one Vect substituent within each molecule of the general formula IA.

In a fourth aspect, the invention covers a method of preparation of an organoselenium compound of the above-mentioned general formula IA, characterized in that it comprises the following essential steps (see Scheme 1):

a) preparing or using a correctly substituted 3-nitro-2-halophenylacetonitrile derivative, then depending on the series considered:
either
b1) hydrolyzing the nitrile derivative to an amide derivative,
c1) transforming this amide derivative into an amine derivative by a transposition reaction using usual methods,
d1) N-acylating this amine derivative using usual procedures;
e1) reacting the latter with a nucleophilic selenium derivative, which may be generated in situ, in the presence of a copper salt, in a polar organic solvent, in order to produce the corresponding benzisoselenazoline derivative,
f1) hydrolysing the heterocyclic derivative thus obtained, if necessary, to the corresponding amine in order to be N-alkylated if necessary using usual procedures;
g1) finally, oxidizing the derivative thus obtained if necessary using usual procedures;
or
b2) reducing the nitrile derivative to an amine derivative with the aid of a reducing agent such as, for example, borane in an ethereal solvent such as, for example, tetrahydrofuran,
c2) N-acylating the amine compound using usual procedures;
d2) reacting the amine compound with a nucleophilic selenium derivative, if necessary generated in situ, in the presence of a copper salt, in a polar organic solvent, in order to produce the corresponding benzisoselenazine derivative,
e2) hydrolyzing the heterocyclic derivative thus obtained if necessary to the corresponding amine in order to be N-alkylated, if necessary, using usual procedures;
f2) finally, oxidizing the derivative thus obtained if necessary using usual procedures;
or
b3) mono- or di-alkylating the nitrile derivative to give an amine derivative,
c3) N-acylating this amine compound using usual procedures;
d3) reacting this amine compound with a nucleophilic selenium derivative, if necessary generated in situ, in the presence of a copper salt, in a polar organic solvent, in order to produce the corresponding benzisoselenazine derivative,
e3) hydrolyzing the heterocyclic derivative thus obtained if necessary to the corresponding amine in order to be N-alkylated if necessary, using usual procedures;
f3) finally, oxidizing the derivative thus obtained if necessary, using usual procedures;

It should be noted that in the framework of the invention, the N-acylation of the amine compound is carried out before proceeding with the reaction with the nucleophilic selenium derivative, since this improves the yield of this synthesis in an unexpected manner.

Another implementation of this procedure is characterized in that the nucleophilic selenium compound is preferably a selenocyanate salt such as, for example, potassium selenocyanate which can be:

either generated in situ from elemental selenium (Se⁰) and a cyanide salt such as, for example, potassium cyanide, or added to the reaction medium as it is.

Yet another particular implementation of the method is characterized in that the copper salt can be a cuprous salt ($Cu^1$), such as, for example, cuprous iodide.

Another implementation of this method is characterized in that the polar organic solvent is preferably dimethylformamide.

Another implementation of this method is characterized in that the oxidizing agent which is optionally used can be a peracid, such as metachloroperbenzoic acid, or hydrogen peroxide.

Other aims, characteristics and advantages of the invention will become clear from the following description which is made with reference to non-limiting examples which are given simply by way of illustration and in no way limit the scope of the invention. In the examples, all the percentages are given as percentages by weight unless stated otherwise. Furthermore, in all the examples, the temperature is expressed in degrees Celsius and the reaction takes place at atmospheric pressure and at room temperature unless stated otherwise.

DESCRIPTION OF FIGURES

In FIG. 2, the compound of the invention of Example 1 (which is also the subject of the test of FIG. 1), is in the presence of various effectors, as follows:

a) the curve with empty circles has been obtained with the compound of the invention of Example 1 used alone;

b) the curve with full squares is obtained with the compound of the invention of Example 1 together with reduced glutathione (GSH) as the effector, being used as a reference;

c) the curve with full circles is obtained with the compound of the invention of Example 1 together with GR NADPH as the effector, GR NADPH being the glutathione reductase enzyme in the presence of its cofactor NADPH alone;

d) the curve with empty squares is obtained with the compound of the invention of Example 1 in the presence of GSH;

e) the curve with full triangles is obtained with the compound of the invention of Example 1 in the presence of both GR NADPH and GSH; and f) the curve with empty triangles is obtained in the presence of the full combination of the effectors GSH, GR NADPH and the compound of the invention of Example 1.

Figure 3:
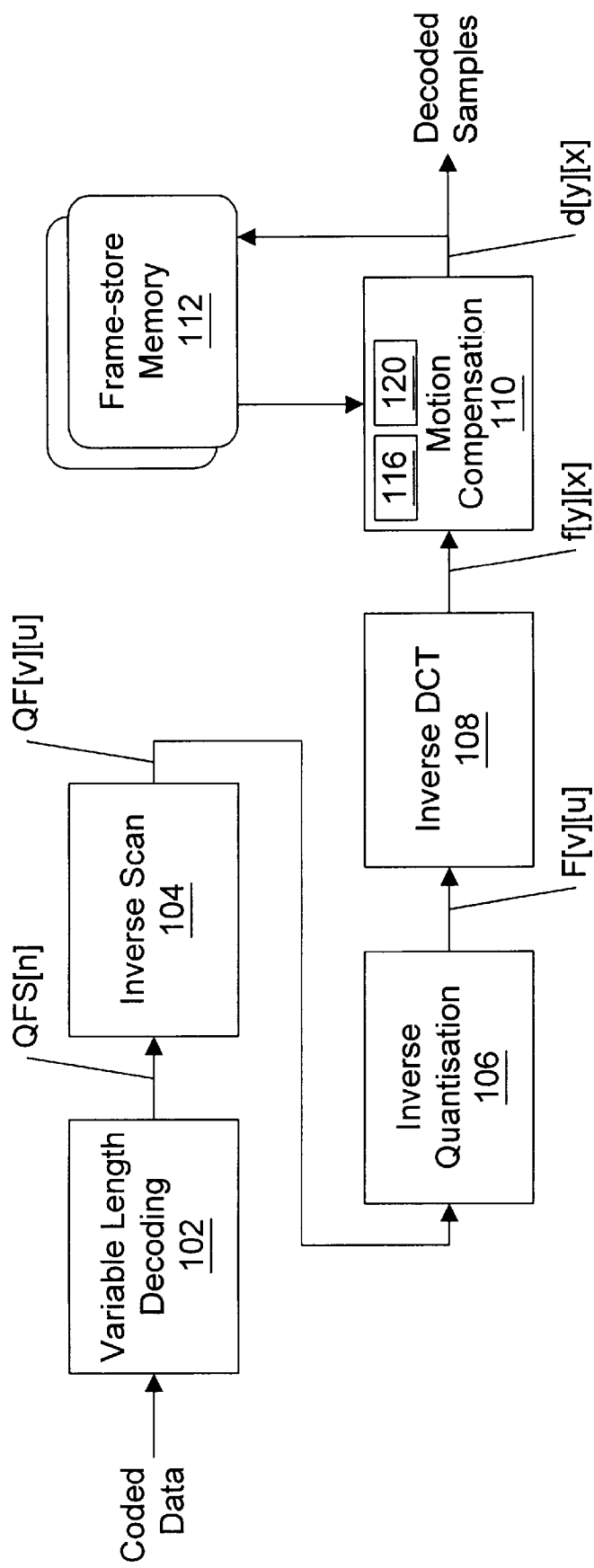

FIG. 3 shows a histogram representing, on the ordinate, the percentage mortality of the HL60 tumor cells after 24 hours incubation with the compound of the invention of Example 1, as a function of concentration of the compound of the invention of Example 1, expressed in micromoles per litre ($\mu$M), along the abcissa. This histogram is obtained from the test of Example 14. The bars with the vertical strokes represent a cellular viability test with the colorant MTT, and the black bars with white dots represent a viability test by coloration with the colorant product trypan blue (TB).

Figure 4:
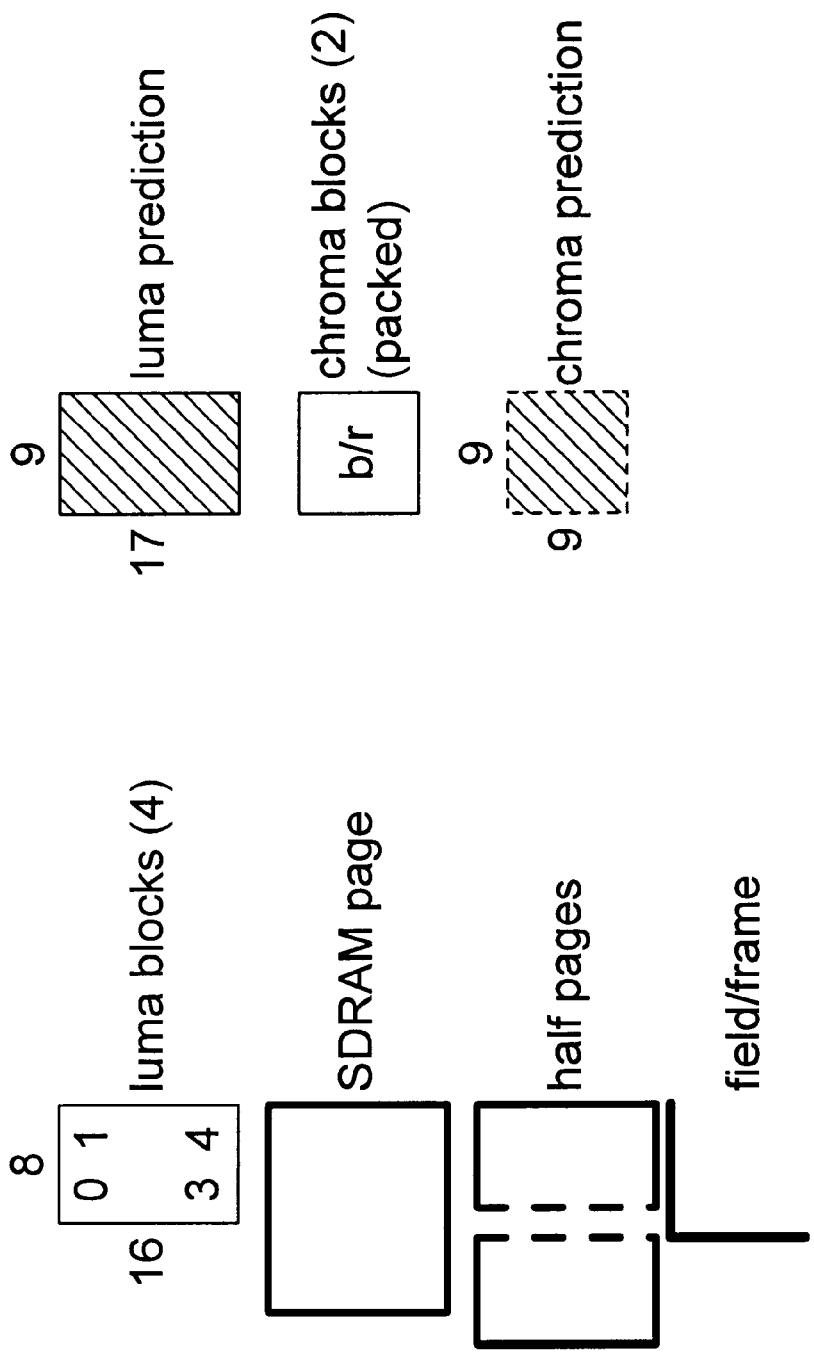

FIG. 4 represents a curve, similar to that of FIG. 3, after 48 hours of incubation.

Figure 5:
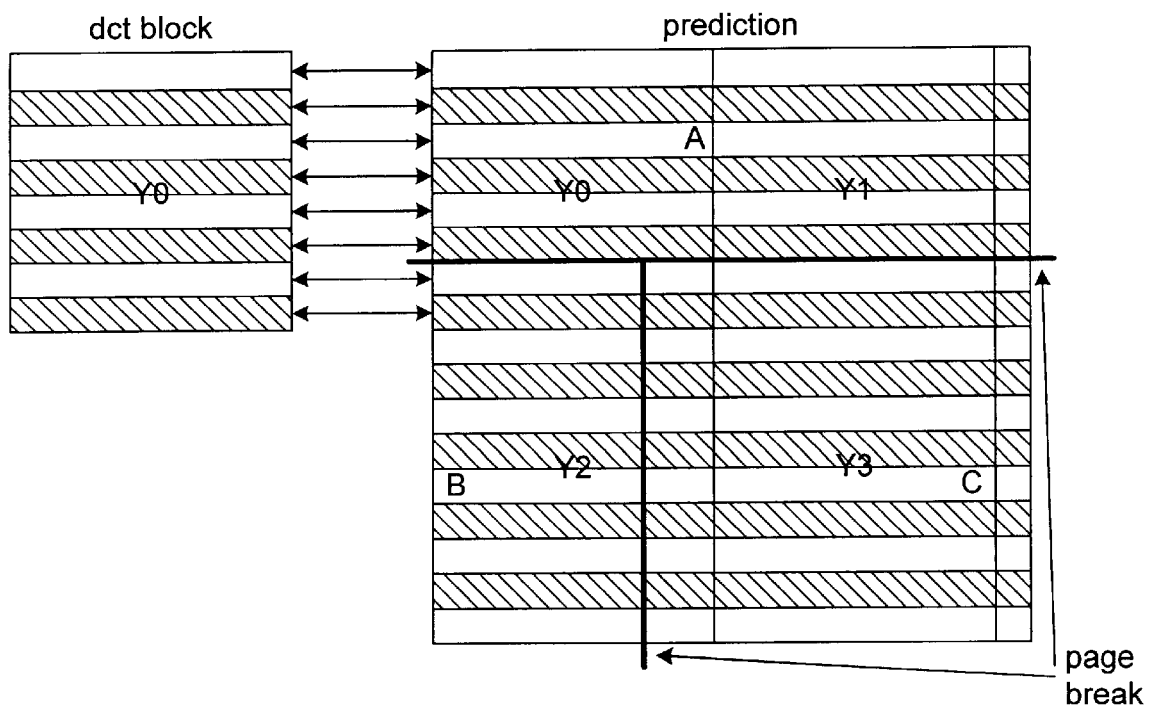

FIG. 5 shows a histogram representing the results of toxicity of the compound of the invention of Example 7, step 1, on breast cancer tumor cells (MCF-7). The various concentrations of the compound of the invention of Example 7, step 1, are expressed along the abcissa in micromoles per litre, and the percentage mortality of these tumor cells is expressed on the ordinate. Black bars represent the toxicity after 24 hours of incubation, whereas white bars represent the toxicity after 48 hours of incubation.

Figure 6:
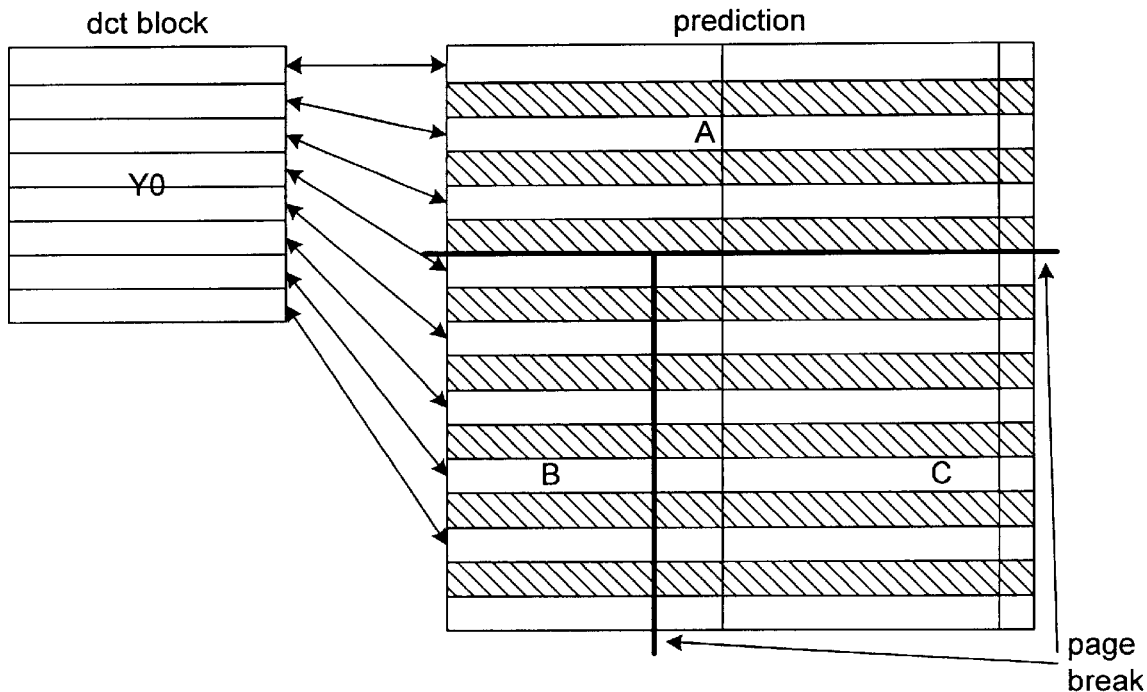

FIG. 6 shows a histogram representing the same test of toxicity as that shown in FIG. 5, but with the compound of the invention of Example 4.

Figure 7:
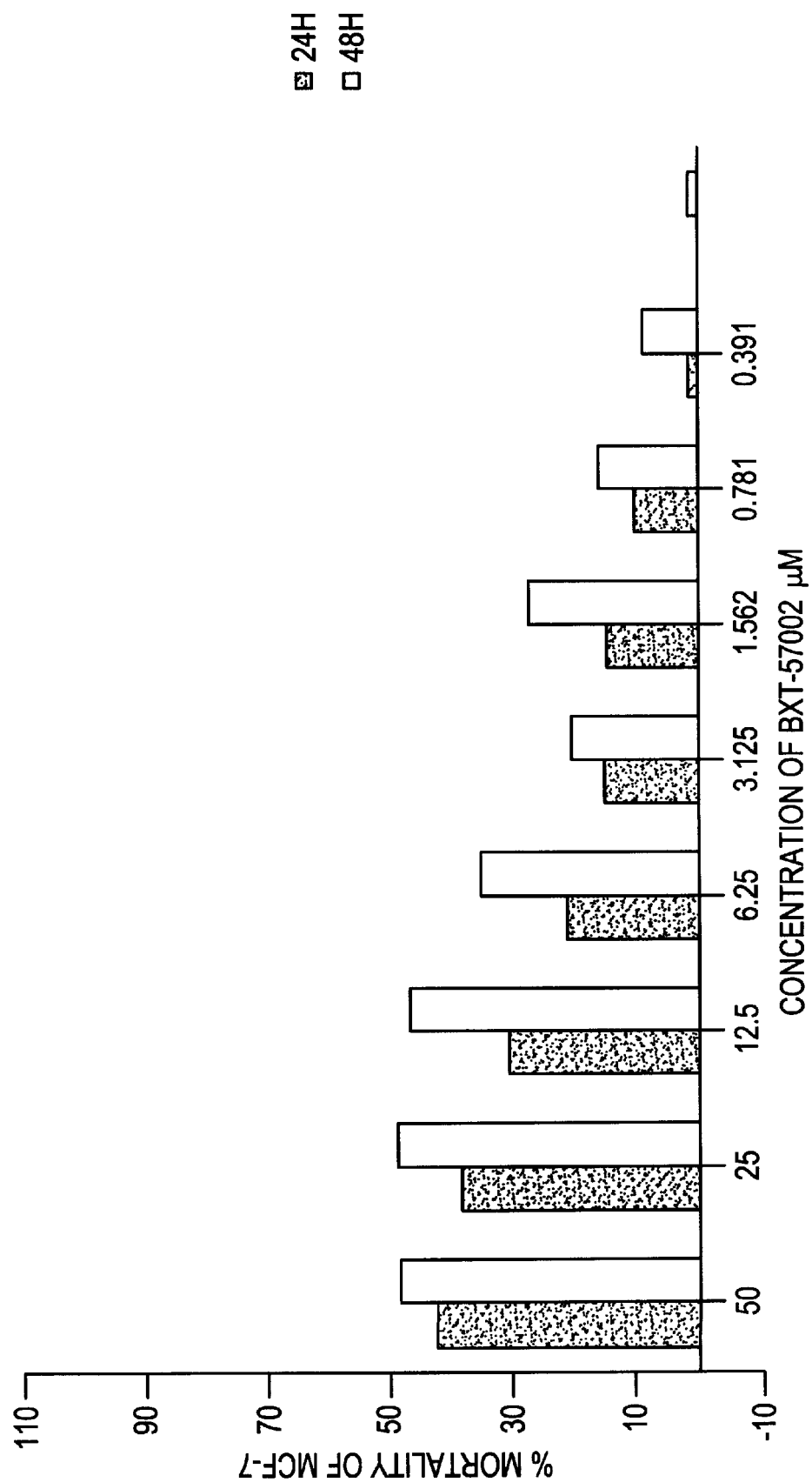

FIG. 7 shows yet another histogram representing the same test of toxicity as those of FIGS. 5 and 6, only this time with the compound of the invention of Example 7, step 1.

Figure 8:
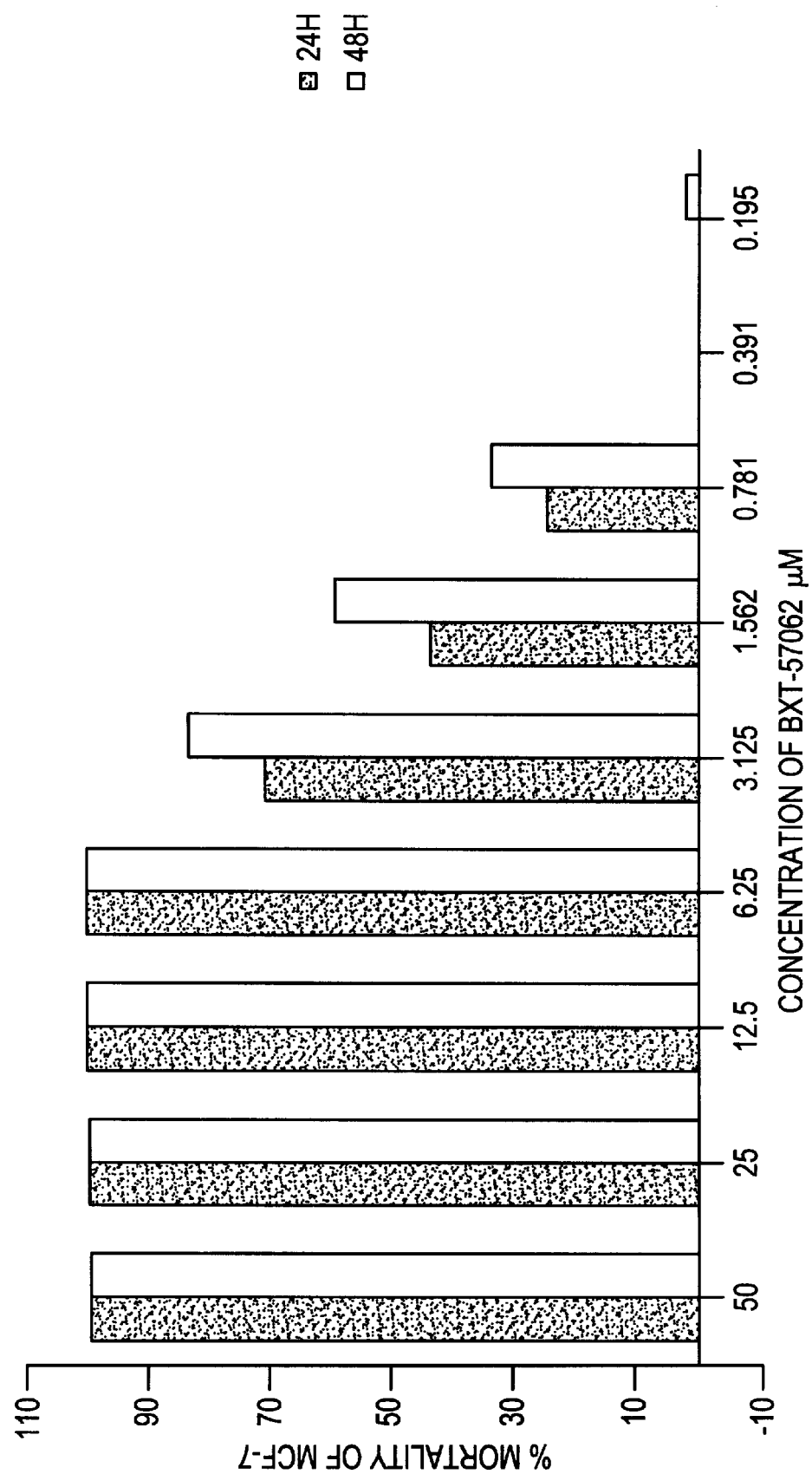
Figure 1:
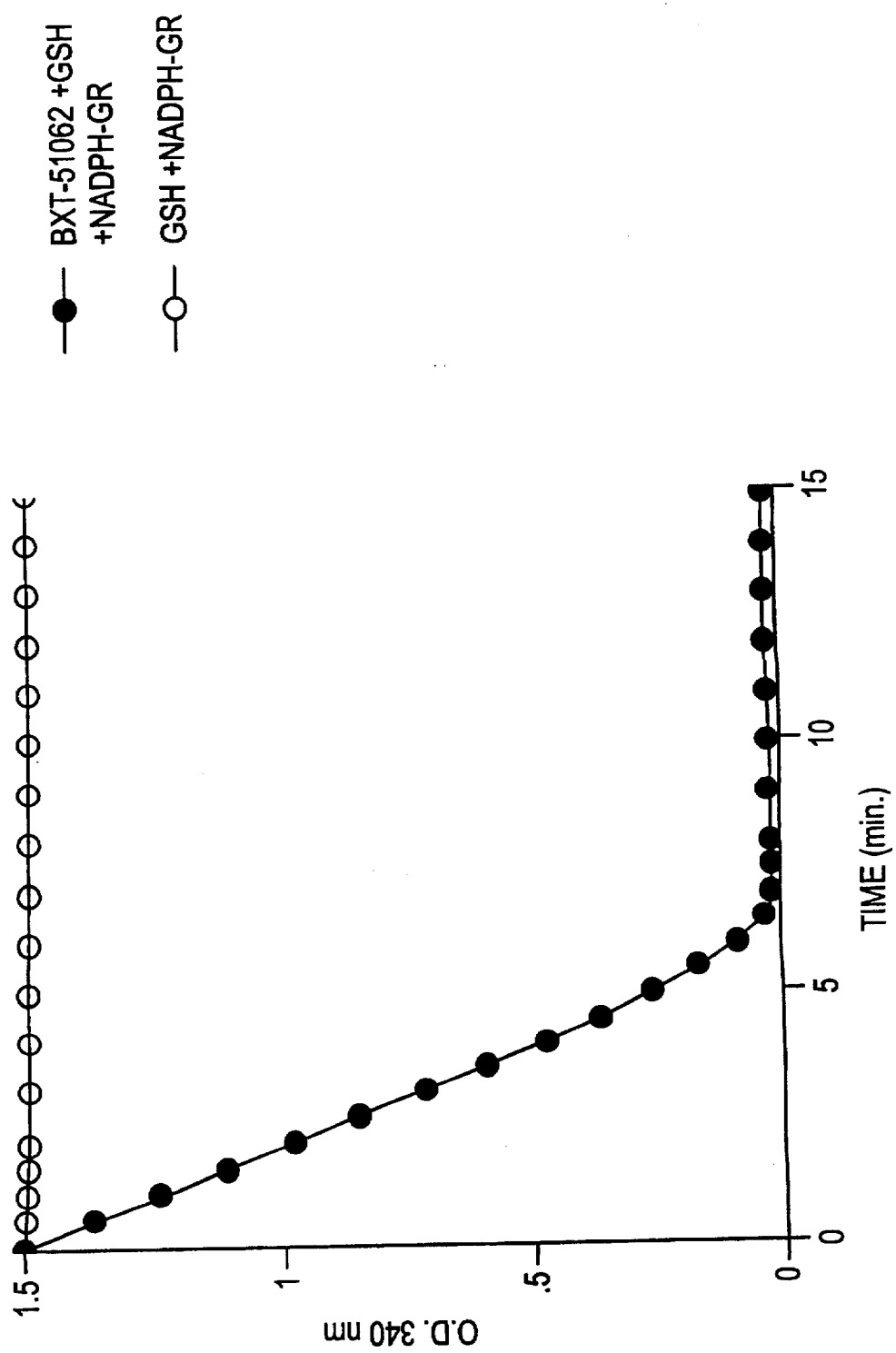
Figure 2:
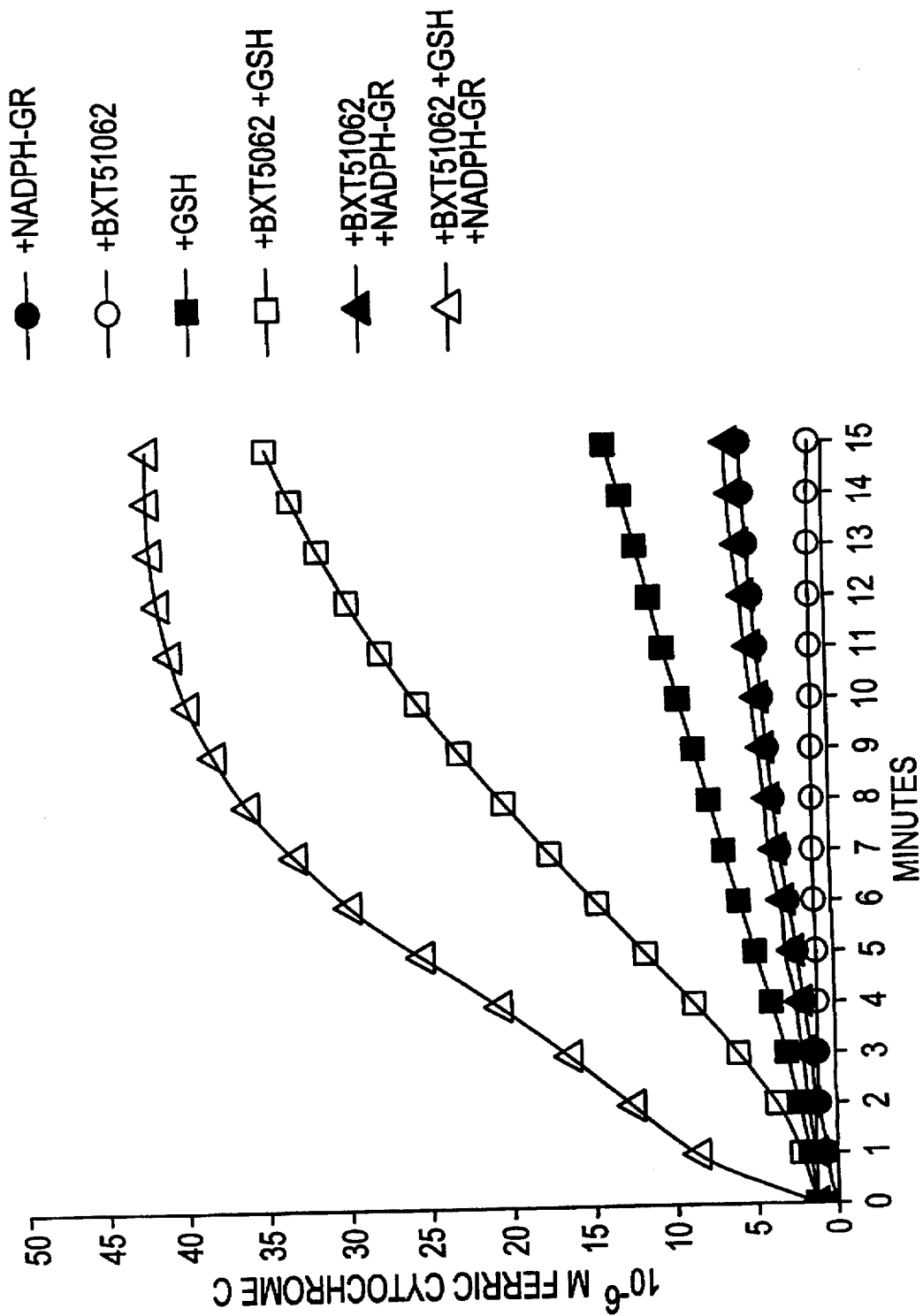
Figure 3:
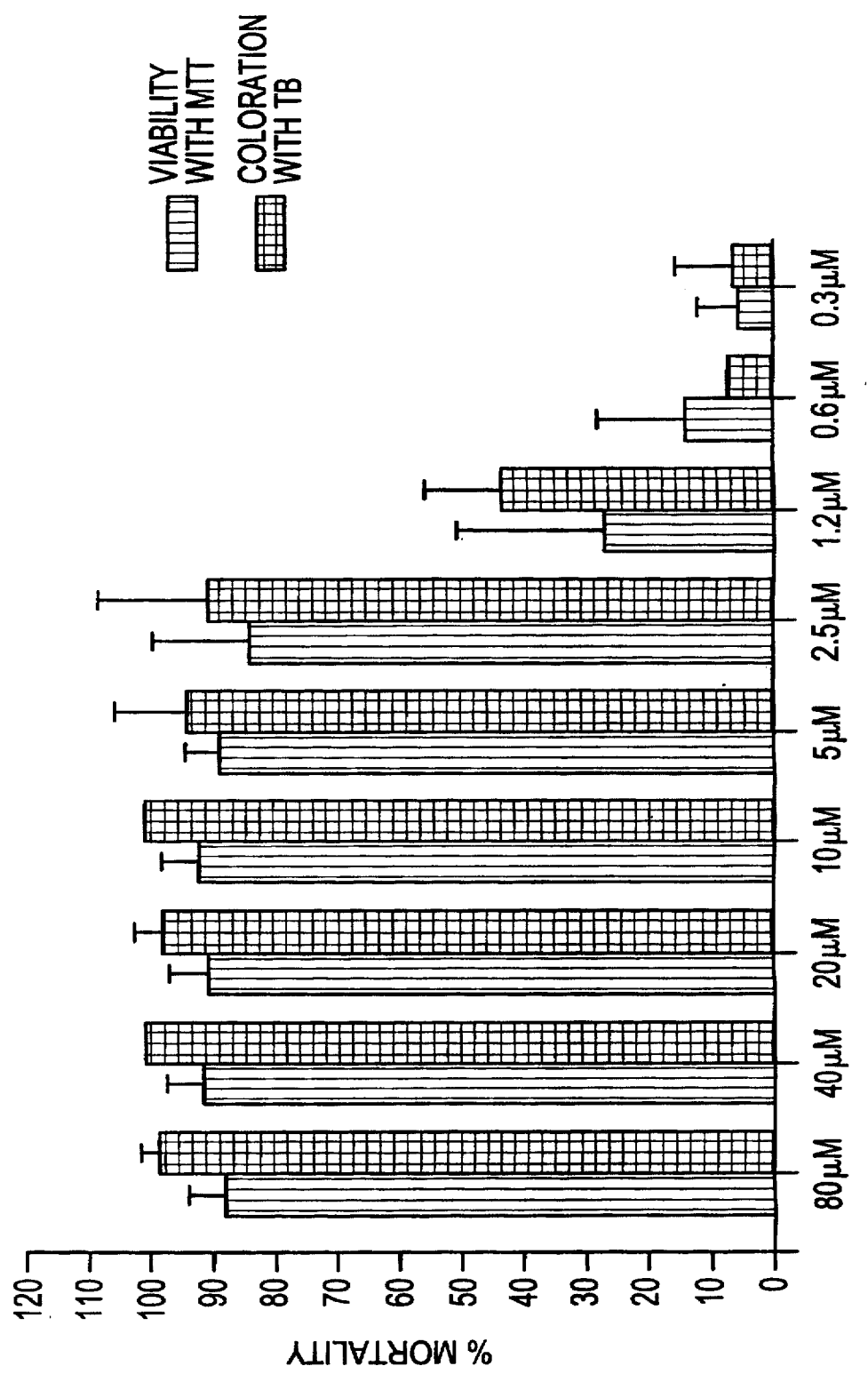
Figure 4:
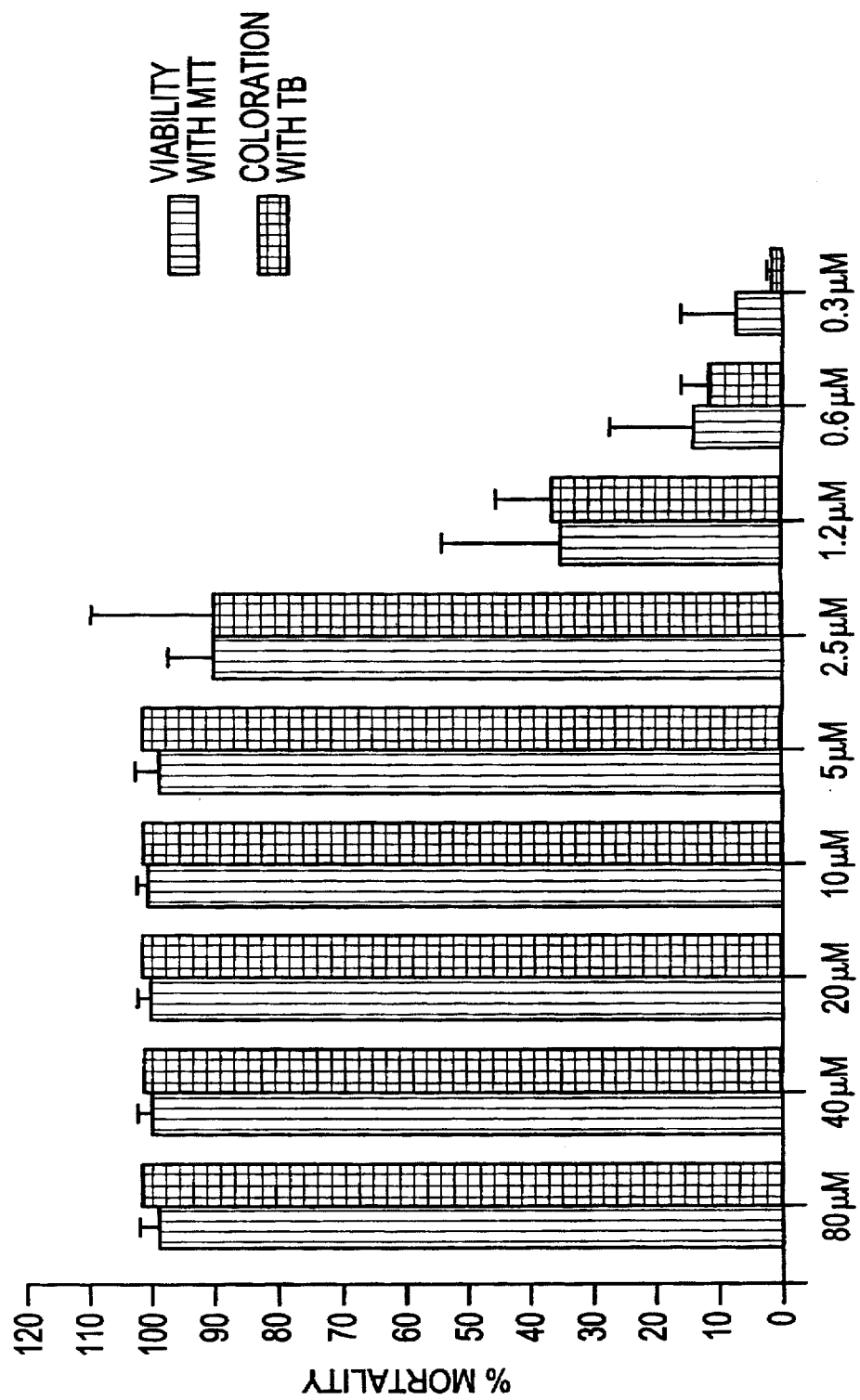
Figure 5:
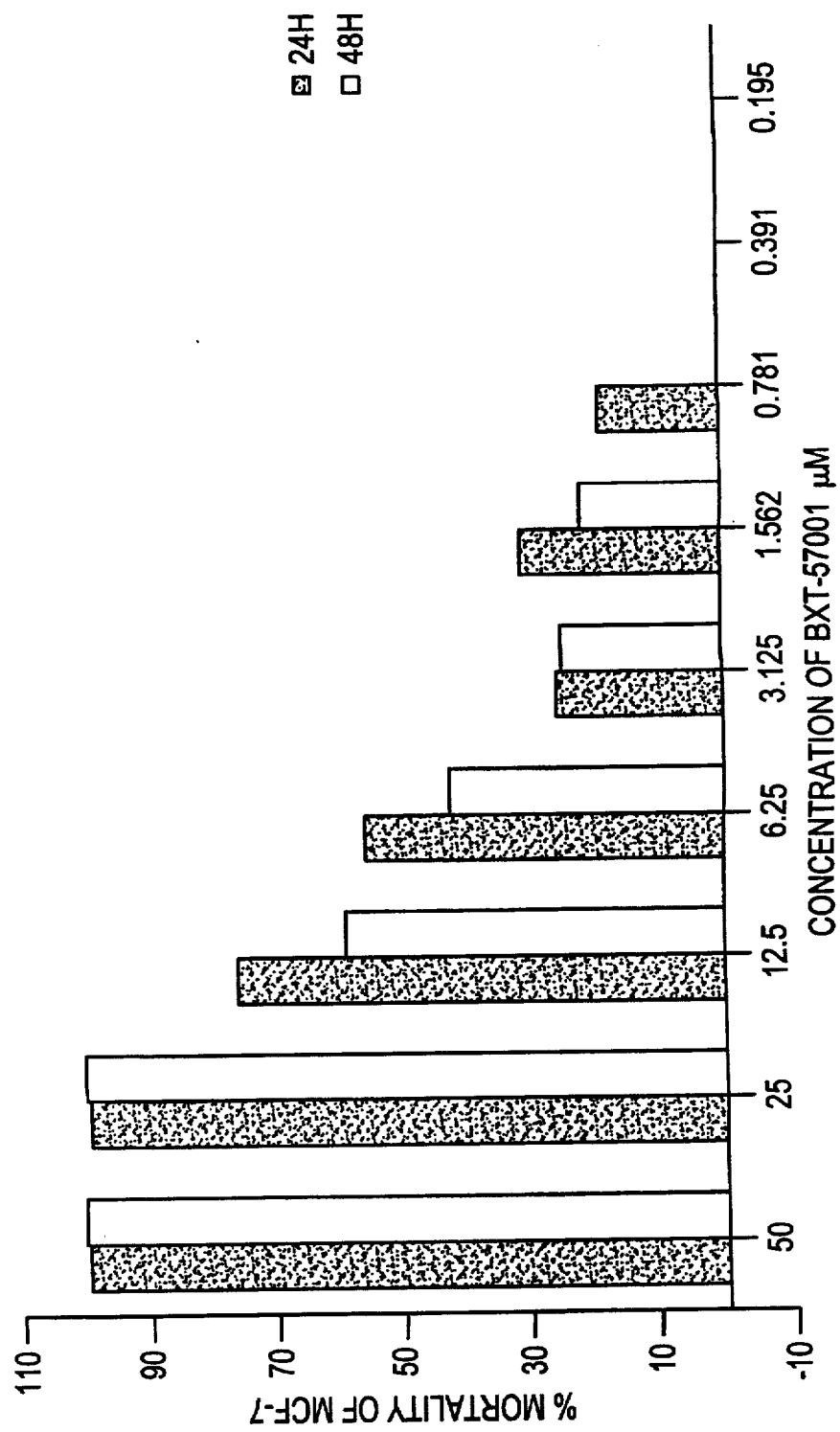
Figure 6:
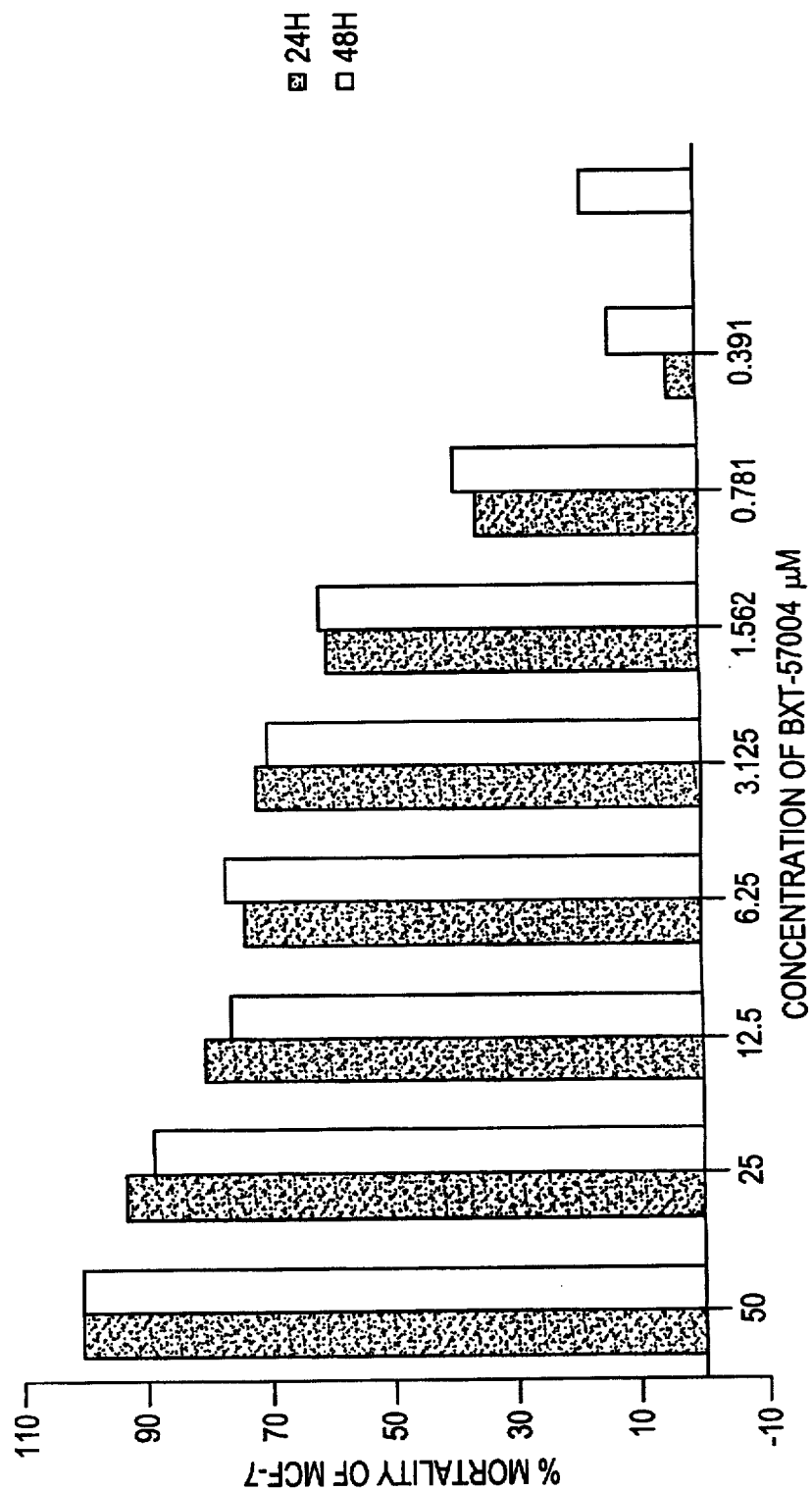
Figure 7:
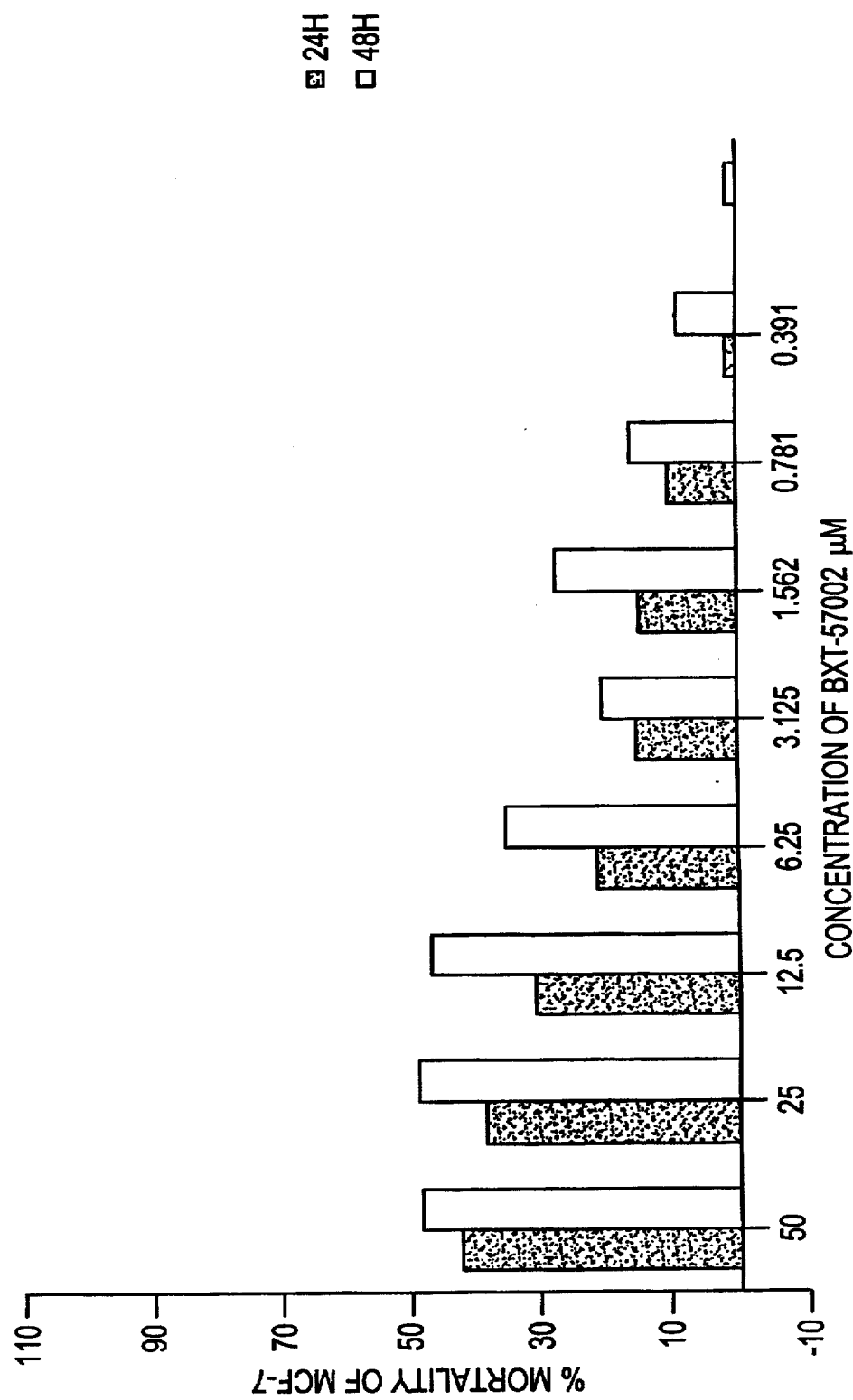
Figure 8:
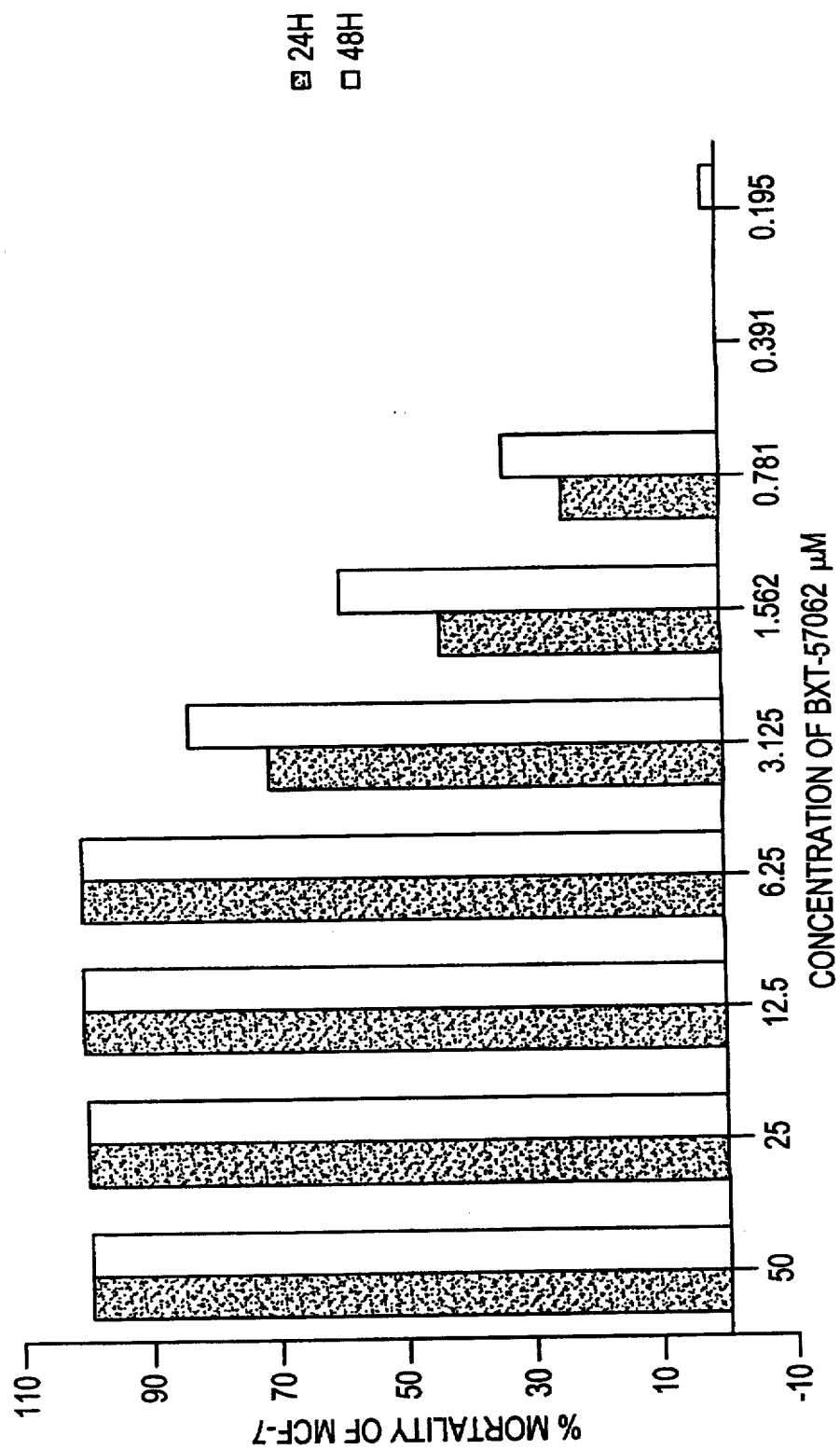

FIG. 8 shows yet another histogram representing the same test of toxicity as those of FIGS. 5 to 7, obtained this time with the compound of the invention of Example 1.

EXPERIMENTAL SECTION

All reactions have been carried out in an inert nitrogen atmosphere unless otherwise stated.

Mass spectra have been recorded on a Nermag R10-10B instrument. Ionisation used either electron impact (EI) at 70 electron-volts, or chemical ionisation (CI) in terbutane.

$^1$H and $^{13}$C NMR spectra were recorded on a Varian Gemini-200 instrument. Chemical shifts are expressed in ppm with respect to tetramethylsilane. Multiplicities are expressed as follows: <<s>> for a singlet, <<br s>> for a broad singlet, <<d>> for a doublet, <<t>> for a triplet, <<q>> for a quadruplet and <<m>> for a multiplet.

Melting points (M. Pt.) were recorded on a Gallenkamp instrument and are uncorrected.

Purification by liquid column chromatography was carried out using Merck® Si 60 $F_{254}$ silica gel.

I. EXAMPLES OF SYNTHESIS OF COMPOUNDS WITH FORMULA IA

Example 1

3,3-Dimethyl-7-nitrobenzisoselenazoline

Step 1. Preparation of 2-bromo-3-nitrobromomethylbenzene.

To a mixture of 2-bromo-3-nitrotoluene (6.48 g, 30 mmol) and N-bromosuccinimide (5.34 g, 30 mmol) in 100 ml of $CCl_4$ is added 2,2'-azobis(2-methylpropionitrile) (AIBN, 300 mg, 1.8 mmol). The mixture thus obtained is heated under reflux for 32 hours and then cooled to room temperature. The solid is filtered and rinsed with $CCl_4$. The filtrate is evaporated to dryness to give a slightly yellow oil (10.1 g). Analysis of the $^1$H NMR spectrum of this crude product indicates that it is a mixture of the expected compound, the dibrominated product and the starting product in a proportion of 57:10:33.

The crude product is used directly in the following step.

Step 2. Preparation of 2-bromo-3-nitrophenylacetonitrile.

The crude brominated product obtained above (10.1 g) is taken up with 75 ml of methanol. Sodium cyanide (1.47 g, 30 mmol) is added in one portion. The mixture is stirred at room temperature for 20 hours. After the evaporation of the solvent, the residue is taken up with 30 ml of $CH_2Cl_2$ and 20 ml of water. The organic phase is separated and the aqueous phase is extracted with $CH_2Cl_2$. The combined organic phases are washed with a saturated aqueous solution of NaCl, dried over $MgSO_4$ and evaporated. The solid residue is triturated with methanol and then filtered and rinsed to give a first batch of the desired compound (1.93 g). The filtrate is concentrated and then triturated with a mixture of ethyl acetate and cyclohexane (1:3). Filtration and rinsing with the same mixture of solvents provide a second batch of the expected compound (0.85 g). The filtrate is again concentrated. The residue is purified by silica gel column chromatography (eluent: $CH_2Cl_2$:cyclohexane, 1:1) to give a third batch of the desired compound. The totality of the isolated product is 3.90 g (54% in two steps from 2-bromo-3-nitrotoluene).

M. Pt. 116° C. $^1$H NMR: 3.94 (s, 2H), 7.53 (t, 1H, J=7.9 Hz), 7.72 (dd, 1H, J=1.4, 7.9 Hz), 7.77 (d, 1H, J=7.9 Hz).

Step 3. Preparation of 2-(2-bromo-3-nitrophenyl)-2-methylpropionitrile.

A suspension of NaH (3.17 g, 60% dispersion in mineral oil, 79.2 mmol) in 70 ml of anhydrous DMF is cooled to −5° C. To this suspension is added a solution of 2-bromo-3-nitrophenylacetonitrile (7.95 g, 32.9 mmol) and iodomethane (8.2 ml, 131.7 mmol) in 30 ml of anhydrous DMF. The reaction medium is stirred at −5° C. for 0.5 hours, at room temperature for 0.5 hours, and then poured into 200 ml of water. The mixture is extracted with ethyl acetate. The combined organic phases are washed with brine, dried over $MgSO_4$ and evaporated. The solid residue (10.93 g) essentially contain the expected product and is used directly in the next step. It can be purified by recrystallization from a mixture of solvents (EtOAc:cyclohexane, 1:3).

M. Pt. 94.5° C. $^1$H NMR: 1.90 (s, 6H), 7.50 (t, 1H, J=8.0 Hz), 7.56 (dd, 1H, J=2.5, 8.0 Hz), 7.66 (d, 1H, J=2.5, 8.0 Hz).

Step 4. Preparation of 2-(2-bromo-3-nitrophenyl)-2-methylpropionamide.

The 2-(2-bromo-3-nitrophenyl)-2-methylpropionitrile obtained above (10.93 g) is dissolved in 250 ml of absolute ethanol. To this solution are successively added 120 ml of a saturated aqueous solution of $K_2CO_3$ and 120 ml of an aqueous solution of $H_2O_2$ (50%). The mixture is stirred vigorously at room temperature for 22 hours. 300 ml of ethyl acetate and 300 ml of water are added. The organic phase is separated and the aqueous phase is extracted with ethyl acetate. The combined organic phases are washed with brine to remove the $H_2O_2$, dried over $MgSO_4$ and evaporated to provide the pure desired compound (8.5 g, 90% in two steps from 2-bromo-3-nitrophenylacetonitrile) as a white solid.

$^1$H NMR: 1.68 (s, 6H), 5.30 (br s, 1H), 5.72 (br s, 1H), 7.48 (m, 2H), 7.65 (m, 1H).

Step 5. Preparation of 1-(2-bromo-3-nitrophenyl)-1-methylethylamine.

The 2-(2-bromo-3-nitrophenyl)-2-methylpropionamide (1.75 g, 6.1 mmol) is mixed with 100 ml of acetonitrile and 100 ml of water. To this mixture is added in one portion [bis(trifluoroacetoxy)iodo]benzene (2.89 g, 6.7 mmol). The reaction medium is stirred at room temperature for 24 hours and then poured into 200 ml of water. The mixture is then extracted with methyl tert-butyl ether. The combined organic phases are washed with brine and then extracted with an aqueous solution of HCl (10%). The combined acidic solutions are washed with methyl tert-butyl ether and, after cooling, are neutralised with an aqueous solution of NaOH (35%). The mixture is extracted with methyl tert-butyl ether. The combined organic phases are washed with a saturated aqueous solution of NaCl, dried over $MgSO_4$ and evaporated to provide the expected amine (1.05 g, 66%) as a slightly yellow oil.

$^1$H NMR: 1.70 (s, 6H), 1.95 (s, 2H), 7.38 (m, 2H), 7.83 (m, 1H).

Step 6. Preparation of 3,3-dimethyl-7-nitrobenzisoselenazoline.

To a solution of 1-(2-bromo-3-nitrophenyl)-1-methylethylamine (10.85 g, 41.9 mmol) in 150 ml of anhydrous DMF is added, at room temperature, KSeCN (6.04 g, 41.9 mmol). The mixture is stirred for 3 minutes to provide a homogeneous solution. CuI (7.98 g, 41.9 mmol) and triethylamine (17.5 ml, 125.8 mmol) are added successively. The reaction medium is stirred at room temperature for 22 hours, then poured into 200 ml of an aqueous solution of CuCN (6.2 g, 68.9 mmol). The mixture is extracted with ethyl acetate. The combined organic phases are washed with brine, dried over $MgSO_4$ and evaporated to provide a red solid. Purification by silica gel column chromatography (eluent: EtOAc:cyclohexane, 1:2) allows one to obtain the desired product (8.45 g, 78%) as a red solid.

M. Pt: 124° C. $^1$H NMR: 1.52 (s, 6H), 3.70 (br s, 1H), 7.26 (dd, 1H, J=1.4, 7.4 Hz), 7.35 (t, 1H, J=7.4 Hz), 8.14 (dd, 1H, J=1.4, 7.4 Hz).

Example 2

N-Acetyl-4,4-dimethyl-8-nitrobenzisoselenazine

Step 1. Preparation of 2-(2-bromo-3-nitrophenyl)-2-methylpropylammonium trifluoroacetate.

The 2-(2-bromo-3-nitrophenyl)-2-methylpropionitrile prepared according to step 3 of Example 1 (1.0 g, 3.7 mmol) is dissolved in 10 ml of anhydrous THF. $BH_3$.THF (10 ml, 1.0 M solution in THF, 10 mmol) is added. The reaction mixture is maintained under reflux for 3 hours before being cooled to room temperature. 12 ml of an aqueous solution of trifluoroacetic acid (50%) is added dropwise. The mixture is heated under relux for 1 hour. The solvents and the trifluoroacetic acid are evaporated. The residue is redissolved in 20 ml of THF and evaporated to dryness. A crude solid product is obtained which contains essentially the desired product and is used directly in the following acetylation step.

Step 2. Preparation of N-acetyl-2-(2-bromo-3-nitrophenyl)-2-methylpropylamine.

To a solution of the above crude ammonium salt dissolved in 10 ml of anhydrous THF is added acetic anhydride (0.52 ml, 5.6 mmol). Triethylamine (2.0 ml, 14.4 mmol) is added dropwise at 0° C. The mixture is stirred at room temperature for 1 hour, then evaporated to dryness. The residue is taken up with 20 ml of ethyl acetate. The organic solution is washed with a saturated aqueous solution of NaCl, dried over $MgSO_4$ and evaporated. The residue is purified by silica gel column chromatography (eluent:

EtOAc:cyclohexane, 2:1) to provide the desired amide (0.97 g, 83% in two steps from 2-(2-bromo-3-nitrophenyl)-2-methylpropionitrile).

MS (EI): 316 (3), 314 (3), 235 (29), 72 (100). $^1$H NMR: 1.55 (s, 6H), 1.91 (s, 3H), 3.91 (d, 2H, J=6.4 Hz), 5.16 (br s, 1H), 7.42 (m, 2H), 7.58 (m, 1H).

Step 3: Preparation of N-acetyl-4,4-dimethyl-8-nitrobenzisoselenazine.

The N-acetyl-2-(2-bromo-3-nitrophenyl)-2-methylpropylamine (158 mg, 0.5 mmol) is dissolved in 3 ml of anhydrous DMF. KSeCN (72 mg, 0.5 mmol) is added. After 3 minutes of stirring at room temperature, CuI (95 mg, 0.5 mmol) and triethylamine (0.21 ml, 1.5 mmol) are added. The mixture obtained is heated at 100° C. for 18 hours, then poured into 8 ml of water. The mixture is then extracted with ethyl acetate. The combined organic phases are washed with brine, dried over $MgSO_4$ and evaporated. The red solid residue is purified by silica gel column chromatography (eluent: EtOAc:cyclohexane, 1:1) to provide the expected product (77 mg, 49%) as a red solid.

M. Pt.: 127° C. MS (EI): 314 (72), 226 (100), 196 (24), 115 (30). $^1$H NMR (this solid exists in the form of a mixture two isomers A and B (60:40) in $CDCl_3$): Isomer A: 1.33 (s, 6H), 2.30 (s, 3H), 3.95 (s, 2H), 7.38 (t, 1H, J=8.1 Hz), 7.82 (dd, 1H, J=1.3, 8.1 Hz), 8.28 (dd, 1H, J=1.3, 8.1 Hz). Isomer B: 1.39 (s, 6H), 2.22 (s, 3H), 3.60 (s, 2H), 7.34 (t, 1H, J=8.4 Hz), 7.78 (dd, 1H, J=1.3, 8.4 Hz), 8.27 (dd, 1H, J=1.3, 8.4 Hz).

Example 3

4,4-Dimethyl-8-nitrobenzisoselenazine

A solution of N-acetyl-4,4-dimethyl-8-nitrobenzisoselenazine (70 mg, 0.22 mmol) of Example 2 dissolved in 1 ml of acetic acid and 1 ml of concentrated hydrochloric acid is heated under reflux for 20 hours. The reaction mixture cooled to 0° C. is neutralized with an aqueous solution of NaOH (10%), then extracted with ethyl acetate. The combined organic phases are washed with a saturated aqueous solution of NaCl, dried over $MgSO_4$ and evaporated. The residue is purified by silica gel column chromatography (eluent: EtOAc:cyclohexane, 1:3) to provide the the desired product (32 mg, 53%) as a yellow solid.

M. Pt.: 108° C. MS (EI): 272 (52), 226 (100), 196 (48), 115 (57). $^1$H NMR: 1.33 (s, 6H), 3.15 (br s, 1H), 3.29 (s, 2H), 7.27 (t, 1H, J=8.3 Hz), 7,75 (dd, 1H, J=1.3, 8.3 Hz), 8.22 (dd, 1H, J=1.3, 8.3 Hz).

Example 4

N-acetyl-3,3-dimethyl-7-nitrobenzisoselenazoline

The 3,3-dimethyl-7-nitrobenzisoselenazoline described in Example 1 (130 mg, 0.5 mmol) is treated with 1 ml of acetic anhydride and 1 ml of pyridine at 60° C. for 1.5 hours. The mixture is then evaporated to dryness. The residue is triturated with a mixture of ethyl acetate and cyclohexane (1:2). The red solid is filtered and rinsed to provide the expected amide (140 mg, 93%).

M. Pt.: 197° C. MS (EI): 300 (21), 285 (25), 243 (100). $^1$H NMR: 1.80 (br s, 6H), 2.32 (br s, 3H), 7.30 (br d, 1H, J=7.8 Hz), 7.42 (t, 1H, J=7.8 Hz), 8.20 (dd, 1H, J=1.2, 7.8 Hz).

Example 5

N-{8-[3,17β-dihydroxyestra-1,3,5(10)-trien-7α-yl] octyl}-3,3-dimethyl-7-nitrobenzisoselenazoline.

Step 1. Preparation of 17β-acetoxy-7α-(oct-7-enyl)estr-4-en-3-one.

To a mixture of 8-bromo-1-octene (6.4 g, 33.5 mmol) and magnesium (0.8 g, 33.3 mmol), is introduced 20 ml of anhydrous THF. A small crystal of $I_2$ is added. The mixture is heated to initiate the reaction. After stirring for 0.5 hours, the mixture is heated under reflux for 1 hour, then diluted with 20 ml of anhydrous THF. It is then cooled to −40° C. CuI (1.90 g, 10.0 mmol) is added in one portion. A solution of 6-dehydro-19-nortestosterone acetate (7.0 g, 22.3 mmol) in 25 ml of anhydrous THF is added dropwise over 15 minutes. The reaction mixture is stirred at −40° C. for 2 hours. Acetic acid (2.0 ml, 35.0 mmol) is introduced at −40° C. 100 ml of brine is then added at room temperature. The mixture is extracted with ethyl acetate. The combined organic phases are washed with brine, dried over $MgSO_4$ and evaporated. The residue is purified by silica gel column chromatography (eluent: EtOAc:cyclohexane, 1:9) to provide firstly the 7α isomer (3.75 g, 39%) then the 7β isomer (2.15 g, 23%).

MS (EI) of 7α isomer: 426 (26), 315 (100). $^1$H NMR of 7α isomer: 0.82 (s, 3H), 2.01 (s, 3H), 0.90–2.53 (m, 31H), 4.59 (dd, 1H, J=7.6, 8.8 Hz), 4.90 (m, 1H), 4.96 (m, 1H), 5.76 (m, 1H), 5.80 (s, 1 H).

Step 2: Preparation of 17β-acetoxy-7α-(oct-7-enyl)estra-1.3.5(10)-trien-3-ol.

To a solution of the preceding estr-4-en-3-one (4.47 g, 10.5 mmol) in 150 ml of acetone are added cyclohexene (26.5 ml, 0.26 mol) and $CuBr_2$ (4.7 g, 21.0 mmol).The mixture obtained is stirred vigorously at room temperature for 20 hours. More $CuBr_2$ (7.05 g, 31.6 mmol) is added in three portions once every three hours. A saturated aqueous solution of $NaHCO_3$ is added. The solvent and the excess cyclohexene are evaporated. The residue is diluted with water, and extracted with ethyl acetate. The combined organic phases are washed with a saturated aqueous solution of NaCl, dried over $MgSO_4$ and evaporated. The residue is purified by silica gel column chromatography (eluent: EtOAc:cyclohenane, 1:9) to provide the desired product (3.76 g, 85%) as a colorless oil.

MS (EI): 424 (100). $^1$H NMR: 0.81 (s, 3H), 0.90–2.35 (m, 24H), 2.05 (s, 3H), 2.68 (d, 1H, J=16.5 Hz), 2.85 (dd, 1H, J=4.8, 16.5 Hz), 4.69 (dd, 1H, 7.6, 8.8 Hz), 4.89 (m, 1H), 4.95 (m, 1H), 5.78 (m, 1H), 6.53 (d, 1H, J=2.5 Hz), 6.61 (dd, 1H, J=2.5, 8.4 Hz), 7.12 (d, 1H, J=8.4 Hz).

Step 3. Preparation of 17β-acetoxy-7α-(8-hydroxyoctyl) estra-1,3,5(10)-trien-3-ol.

To a solution of 17β-acetoxy-7α-(oct-7-enyl)estra-1,3,5 (10)-trien-3-ol (0.38 g, 0.90 mmol) in 10 ml of anhydrous THF is added 9-BBN (5 ml, 0.5 M solution in THF, 2.5 mmol). The mixture is stirred at room temperature for 3 hours. 3 ml of an aqueous solution of KOH (3N) and 3 ml of an aqueous solution of hydrogen peroxide (30%) are added successively. The reaction medium is stirred for 18 hours then neutralised to pH 7 with an aqueous solution of HCl (1N). The mixture is extracted with ethyl acetate. The combined organic phases are washed with a saturated aqueous solution of NaCl, dried over $MgSO_4$ and evaporated. The residue is purified by silica gel column chromatography (eluent: EtOAc:cyclohexane, 1:4) to provide the expected diol (0.214 g, 54%) as a colourless oil.

MS (EI): 442 (72), 253 (46), 157 (62). $^1$H NMR: 0.82 (s, 3H), 0.90–2.40 (m, 26H), 2.05 (s, 3H), 2.68 (d, 1H, J=16.5

Hz), 2.85 (dd, 1H, J=4.8, 16.5 Hz), 3.64 (t, 2H, J=6.5 Hz), 4.70 (t, 1H, J=8.8 Hz), 6.12 (br s, 1H), 6.55 (d, 1H, J=2.2 Hz), 6.64 (dd, 1H, J=2.2, 8.4 Hz), 7.13 (d, 1H, J=8.4 Hz).

Step 4. Preparation of 17β-acetoxy-3-benzoyloxy-7α-(8-hydroxyoctyl)estra-1,3,5(10)-triene.

An aqueous solution of NaOH (0.75 ml, 1N, 0.75 mmol) is added to a solution of the above diol (214 mg, 0.48 mmol) in acetone cooled to −5° C. To the resulting mixture is added dropwise benzoyl chloride (87 ml, 0.75 mmol). The mixture is stirred for 10 minutes at −5° C. 10 ml of water and 10 ml of a saturated aqueous solution of $NaHCO_3$ are added. The mixture is extracted with ethyl acetate. The combined organic phases are washed with a saturated aqueous solution of NaCl, dried over $MgSO_4$ and evaporated. The residue is purified by silica gel column chromatography (eluent: EtOAc:cyclohexane, 1:2) to provide the expected product (242 mg, 92%) as a colorless oil.

MS (EI): 546 (33), 486 (30), 441 (21), 105 (100). $^1$H NMR: 0.82 (s, 3H), 0.90–2.50 (m, 26H), 2.06 (s, 3H), 2.75 (d, 1H, J=16.5 Hz), 2.92 (dd, 1H, J=2.3, 16.5 Hz), 3.60 (t, 2H, J=6.5 Hz), 4.69 (t, 1H, J=8.8 Hz), 6.91 (d, 1H, J=2.3 Hz), 6.96 (dd, 1H, J=2.3, 8.4 Hz), 7.34 (d, 1H, J=8.4 Hz), 7.50 (m 2H), 7.61 (m, 1H), 8.19 (m, 2H).

Step 5. Preparation of 17β-acetoxy-3-benzoyloxy-7α-(8-methanesulfonyloxyoctyl)estra-1,3,5(10)-triene.

To a solution of 17β-acetoxy-3-benzoyloxy-7α-(8-hydroxyoctyl)estra-1,3,5(10)-triene (242 mg, 0.44 mmol) in 5 ml of $CH_2Cl_2$ cooled to 0° C. is added triethylamine (92 ml, 0.66 mmol). Methanesulfonyl chloride (38 ml, 0.48 mmol) is added dropwise. The mixture is stirred at 0° C. for 30 minutes, then at room temperature for 30 minutes. The solvent is evaporated, the residue is mixed with water, then extracted with ethyl acetate. The combined organic phases are washed with a saturated aqueous solution of NaCl, dried over $MgSO_4$ and evaporated to dryness to provide a colorless oil which contains essentially the desired product (0.53 g). This oil is used directly in the next step.

$^1$H NMR: 0.82 (s, 3H), 0.90–2.50 (m, 26H), 2.05 (s, 3H), 2.75 (d, 1H, J=16.5 Hz) 2.92 (dd, 1H, J=4.8, 16.5 Hz), 3.00 (s, 3H), 4.21 (t, 2H, J=6.6 Hz), 4.76 (t, 1H, 8.7 Hz), 6.90 (d, 1H, J=2.40 Hz), 6.98 (dd, 1H, J=2.4, 8.4 Hz), 7.35 (d, 1H, J=8.4 Hz), 7.50 (m, 2H), 7.61 (m, 1H), 8.20 (m, 2H).

Step 6. Preparation of N-{8-[17β-acetoxy-3-benzoyloxyestra-1,3,5(10)-trien-7α-yl]octyl}-3,3-dimethyl-7-nitroisoselenazoline.

Following the method of alkylation of 3,3-dimethyl-7-nitrobenziso-selenazoline described in step 1 of Example 8, the expected product is obtained as a deep red solid from the preceeding mesylate with a yield of 61% [calculated in two steps from 17β-acetoxy-3-benzoyloxy-7α-(8-hydroxyoctyl) estra-1,3,5(10)-triene].

MS (CI, tBuH): 787 (100). $^1$H NMR: 0.84 (s, 3H), 1.53 (s, 6H), 2.06 (s, 3H), 0.90–2.50 (m, 26H), 2.80 (m,4H), 4.71 (t, 1H, J=7.8 Hz), 6.92 (d, 1H, J=2.3 Hz), 6.97 (dd, 1H, J=2.3, 8.4 Hz), 7.31 (m, 3H), 7.50 (m, 2H), 7.60 (m, 1H), 8.18 (m, 3H).

Step 7: Preparation of N-{8-[3.17β-dihydroxyestra-1,3,5(10)-trien-7α-yl]octyl}-3,3-dimethyl-7-nitrobenzisoselenazoline.

N-{8-[17β-acetoxy-3-benzoyloxyoestra-1,3,5(10)-trien-7α-yl]octyl}-3,3-dimethyl-7-nitrobenzisoselenazoline (115 mg, 0.15 mmol) is dissolved in 2 ml of THF and 1 ml of methanol. To the obtained mixture is then added an aqueous solution of NaOH (1 ml, 1N, 1.0 mmol). The reaction medium is stirred at room temperature for 22 hours, then neutralized with an aqueous solution of HCl (1N). The mixture is extracted with ethyl acetate. The combined organic phases are washed with a saturated aqueous solution of NaCl, dried over $MgSO_4$ and evaporated. The residue is purified by silica gel column chromatography (eluent: EtOAc:cyclohexane, 1:3) to provide the expected product (95 mg, 94%) as a deep red solid.

M. Pt.: 95° C. MS (EI): 640 (18), 625 (100), 395 (31), 278 (62). $^1$H NMR: 0.78 (s, 3H), 1.55 (s, 6H), 0.90–2.35 (m, 26H), 2.78 (m, 4H), 3.75 (t, 1H, J=8.4 Hz), 6.54 (d, 1H, J=2.6 Hz), 6.62 (dd, 1H, J=2.6, 8.4 Hz), 7.13 (d, 1H, J=8.4 Hz), 7.30 (dd, 1H, J=1.7, 7.4 Hz), 7.36 (t, 1H, J=7.4 Hz), 8.17 (dd, 1H, J=1.7, 7.4 Hz).

Example 6

N-{8-[3,17β-dihydroxyestra-1,3,5(10)-trien-7α-yl] octanoyl}-3,3-dimethyl-7-nitrobenzisoselenazoline Step 1: Preparation of 8-(17β-acetoxy-3-benzoyloxyestra-1, 3,5(10)-trien-7α-yl)octanoic acid.

To a solution of 17β-acetoxy-3-benzoyloxy-7α-(8-hydroxyoctyl)-estra-1,3,5(10)-triene (0.74 g, 1.4 mmol), described in step 4 of Example 5, in 10 ml of acetone cooled to 0° C. is added dropwise a solution of Jones' Reagent (aqueous solution of chromic acid, 8N, 0.85 ml, 6.8 mmol). After stirring for 15 minutes, 0.3 ml of isopropanol is added and the mixture is evaporated to dryness. Brine is added to the residue. The mixture is extracted with ethyl acetate. The combined organic phases are washed with a saturated aqueous solution of NaCl, dried over $MgSO_4$ and evaporated. The residue is purified by silica gel column chromatography (eluent: EtOAc:cyclohexane, 1:1) to provide the expected acid (0.53 g, 70%) as a white solid.

MS (CI, t-BuH): 560 (66), 455 (100). $^1$H NMR: 0.84 (s, 3H), 2.07 (s, 3H), 0.90–2.50 (m, 26H), 2.76 (d, 1H, J=17.1 Hz), 2.93 (dd, 1H, J=4.3, 17.1 Hz), 4.72 (t, 1H, J=8.1 Hz), 6.92 (d, 1H, J=2.3 Hz), 6.97 (dd, 1H, J=2.3, 8.5 Hz), 7.33 (d, 1H, J=8.5 Hz), 7.50 (m, 2H), 7.62 (m, 1H), 8.19 (m, 2H).

Step 2: Preparation of N-{8-[17β-acetoxy-3-benzoyloxyestra-1,3,5(10)-trien-7α-yl]octanoyl}-3,3-dimethyl-7-nitrobenzisoselenazoline.

To a solution of the above acid (220 mg, 0.39 mmol) in 5 ml of $CH_2Cl_2$ are added sulfonyl chloride (48 ml, 0.66 mmol) and 5 ml of anhydrous DMF. The mixture is stirred at room temperature for 1 hour, heated under reflux for 0.5 hours, then evaporated to dryness. The residue is taken up with 5 ml of $CH_2Cl_2$, evaporated again to dryness and then dissolved in 3 ml of $CH_2Cl_2$. The solution obtained is added dropwise, at room temperature, to a solution of 3,3-dimethyl-7-nitrobenzisoselenazoline of Example 1 (86 mg, 0.33 mmol) and triethylamine (70 ml, 0.5 mmol) in 5 ml of $CH_2Cl_2$. The mixture is stirred for 1 hour then evaporated to dryness. The residue is purified directly by silica gel column chromatography (eluent: EtOAc:cyclohexane, 1:4) to provide the expected product (265 mg, 84%) as a red solid.

MS (CI, t-BuH): 801 (100), 153 (20), 139 (21). $^1$H NMR: 0.82 (s, 3H), 1.82 (br s, 6H), 2.04 (s, 3H), 0.90–2.50 (m, 26H), 2.76 (d, 1H, J=17.1 Hz), 2.92 (dd, 1H, J=4.6, 17.1 Hz), 4.69 (dd, 1H, J=7.7, 8.4 Hz), 6.90 (d, 1H, J=2.4 Hz), 6.96 (dd, 1H, J=2.4, 8.4 Hz), 7.26–7.42 (m, 3H), 7.48 (m, 2H), 7.61 (m, 1H), 8.19 (m, 3H).

Step 3: Preparation of N-{8-[3,17β-dihydroxyestra-1,3,5 (10)-trien-7α-yl]octanoyl}-3,3-dimethyl-7-nitrobenzisoselenazoline.

Following the method described in step 7 of Example 5, the above-mentioned amide is saponified to provide the expected final product as a red solid with a yield of 79%.

M. Pt.: 128° C. MS (CI, t-BuH): 655 (100), 115 (26). $^1$H NMR 0.77 (s, 3H), 0.90–2.50 (m, 32H), 2.53 (br s, 1H), 2.70 (d, 1H, J=17.1 Hz), 2.85 (dd, 1H, J=4.3, 17.1 Hz), 3.76 (t, 1H, J=7.9 Hz), 6.02 (br s, 1H), 6.58 (d, 1H, J=2.6 Hz), 6.65 (dd, 1H, J=2.6, 8.4 Hz), 7.14 (d, 1H, J=8.4 Hz), 7.34 (br d, 1H, J=7.7 Hz), 7.45 (t, 1H, J=7.7 Hz), 8.23 (dd, 1H, J=1.1, 7.7 Hz).

Example 7

N-{2-[4-(1,2-diphenylbut-1-en-1-yl)phenoxy]ethyl}3,3-dimethyl-7-nitrobenzisoselenazoline Step 1: Preparation of N-(2-hydroxyethyl)-3,3-dimethyl-7-nitrobenzisoselenazoline.

To a solution of 3,3-dimethyl-7-nitrobenzisoselenazoline (1.03 g, 4 mmol) in 2-bromoethanol (20 ml, 280 mmol, 70 eq.) is added in one portion 1,8-diaza-bicyclo[5.4.0]undec-7-ene, DBU (2.99 ml, 20 mmol, 5 eq.). The reaction medium is then heated to 70° C. and stirring is continued for 6 hours at this temperature. Initially orange, the solution progressively turns brown. After having removed the excess bromoethanol by distillation (0.1 mbar, 60° C.), the residue is taken up with 50 ml of ethyl acetate and extracted with 10 ml of water (twice). After evaporation of the ethyl acetate, the oil obtained is purified by silica gel column chromatography (eluent: ethyl acetate:cyclohexane, 1:2 then 1:1).

The desired compound is obtained with a yield of 84% as brown crystals.

$^1$H NMR: 1.52 (s, 6H), 2.5 (m, 1H —OH), 3.04 (t, 2H, J=5.0 Hz), 3.72 (m, 2H), 7.32 (m, 2H), 8.16 (dd, 1H, J=1.9, 7.3 Hz). $^{13}$C NMR: 25.50, 54.48, 62.12, 72.51, 123.90, 127.77, 128.77, 138.34, 144.16, 151.39.

Step 2: Preparation of N-(2-methanesulfonyloxyethyl)-3,3-dimethyl-7-nitroisoselenazoline.

To a solution of the alcohol, prepared in step 1 above, (0.297 g, 1 mmol) in 10 ml of THF containing triethylamine (0.15 ml, 1.1 mmol) cooled to 0–5° C. by an ice bath, is added dropwise methanesulfonyl chloride (0.085 ml, 1.1 mmol); the ice bath is removed and stirring is continued for 1 hour at room temperature. After the addition of 10 ml of water, the reaction medium is extracted with 20 ml of ethyl acetate (twice). The organic phases are combined, washed with 10 ml of a saturated aqueous solution of NaCl, then dried over MgSO$_4$ before being evaporated.

After silica gel column chromatography (eluent: ethyl acetate:cyclohexane, 1:2) the mesylate (0.36 g, 96%) is obtained as brown crystals.

$^1$H NMR: 1.54 (s, 6H), 3.07 (s, 3H), 3.20 (t, 2H, J=5.5 Hz), 4.36 (t, 2H, J=5.5 Hz). $^{13}$C NMR: 25.71, 38.09, 52.91, 70.09, 73.14, 124.04, 128.10, 128.97, 138.05, 144.49, 150.91.

Step 3: Preparation of N-{2-[4-(1,2-diphenylbut-1-en-1-yl)phenoxy]ethyl}-3,3-dimethyl-7-nitroisoselenazoline.

To a suspension of sodium hydride (8 mg, 60% dispersion in mineral oil, 0.2 mmol) in 2 ml of THF, under nitrogen, at room temperature, is added dropwise a solution of (Z)-1,2-diphenyl-1-(4-hydroxyphenyl)but-1-ene (50 mg, 0.167 mmol) in 2 ml of THF. After 1 hour of stirring at room temperature, the yellow solution obtained is treated with the mesylate derivative of the selenazoline (76 mg, 0.2 mmol) prepared above. The reaction mixture is heated under reflux for 48 hours then, after cooling and neutralization with a saturated solution of NH$_4$Cl, it is extracted with 10 ml of ethyl acetate and washed with a saturated solution of NaCl; the organic phase is dried and then evaporated before being chromatographed on a silica gel column (eluent: ethyl acetate:cyclohexane, 1:9).

The desired compound (70 mg, 72%) is obtained as brown crystals.

MS (EI): 583 (15), 568 (100), 270 (22). $^1$H NMR: 0.94 (t, 3H, J=7.4 Hz), 1.57 (s, 6H), 2.48 (q, 2H, J=7.4 Hz), 3.27 (t, 2H, J=5.8 Hz), 4.24 (t, 2H, J=5.8 Hz), 6.62 (d, 2H, J=8.9 Hz), 6.84 (d, 2H, J=8.9 Hz), 7.23 (m, 12H), 8.80 (dd, 1H, J=1.8, 7.3 Hz).

Example 8

N-{8-[4-(1,2-diphenylbut-1-en-1-yl)phenoxy]octyl}-3,3-dimethyl-7-nitrobenzisoselenazoline Step 1: Preparation of N-(8-hydroxyoctyl)-3,3-dimethyl-7-nitrobenzisoselenazoline.

A mixture of 3,3-dimethyl-7-nitrobenzisoselenazoline (2.57 g, 10 mmol), 8-bromo-octanol (3.4 ml, 20 mmol), tetra-n-butylammonium iodide (3.69 g, 10 mmol) and bis (N-dimethylamino)naphthalene (3.20 g, 15 mmol) is stirred, at 110° C. for 12 hours. After cooling and the addition of 20 ml of water, the resulting solution is extracted with 40 ml of ethyl acetate (twice). The organic phases are combined, washed with 20 ml of a saturated solution of NaCl, dried over MgSO$_4$ and evaporated.

Silica gel column chromatography (eluent: ethyl acetate:cyclohexane, 1:3) permits obtaining a very viscous brown oil (2.11 g, 55%).

$^1$H NMR: 1.20–1.70 (m, 19H), 2.80 (m, 2H), 3.61 (s, 2H, J=6.5 Hz), 7.31 (m, 2H), 8.15 (dd, 1H, J=1.6, 7.4 Hz).

Step 2: Preparation of N-{8-[4-(1,2-diphenylbut-1-en-1-yl)phenoxy]octyl}-3,3-dimethyl-7-nitrobenzisoselenazoline.

To a solution of (Z)-1,2-diphenyl-1-(4-hydroxyphenyl) but-1-ene phenate (64 mg, 0.21 mmol) is added, at room temperature and dropwise, a solution of N-(8-hydroxyoctyl)-3,3-dimethyl-7-nitrobenzisoselenazoline mesylate (130 mg, 0.28 mmol), prepared in step 2 of Example 7. The reaction mixture is held under reflux of THF for 36 hours then treated according to the protocol of step 3 of Example 7.

After chromatography (eluent: ethyl acetate: cyclohexane, 1:9 then 1:5), the expected product (112 mg, 80%) is formed as brown crystals.

$^1$H NMR of the mesylate: 1.25–1.80 (m, 12H), 1.53 (s, 6H), 2.82 (m, 2H), 2.99 (s, 3H), 4.24 (t, 2H, J=6.3 Hz), 7.33 (m, 2H), 8.19 (dd, 1H, J=1.5, 7.0 Hz). MS (EI) of the selenazoline: 668 (32), 493 (85), 305 (100). $^1$H NMR of the selenazoline: 0.94 (t, 3H, J=7.5 Hz), 1.25–1.80 (m, 12H), 1.43 (s, 6H), 2.49 (q, 2H, J=7.5 Hz), 2.83 (m, 2H), 4.08 (t, 2H, J=6.1 Hz), 6.64 (d, 2H, J=8.5 Hz), 6.87 (d, 2H, J=8.5 Hz), 7.10–7.05 (m, 12H), 8.20 (dd, 1H, J=1.7, 7.2 Hz).

Example 9

N-{2-[4-(1,2-diphenylbut-1-en-1-yl)phenoxy]acetyl}-3,3-dimethyl-7-nitrobenzisoselenazoline Step 1: Preparation of N-(chloroacetyl)-3,3-dimethyl-7-nitrobenzisoselenazoline.

To a solution of 3,3-dimethyl-7-nitrobenzisoselenazoline (1.28 g, 5 mmol), in 20 ml of anhydrous THF, containing triethylamine (0.83 ml, 6 mmol), cooled to 5° C. by an ice bath, is added dropwise chloroacetyl chloride (0.48 ml, 6 mmol). The dark brown reaction medium lightens rapidly, becoming luminous orange; as soon as the addition of the acid chloride is complete, a considerable precipitate, corresponding to triethylammonium chloride, appears. The amide formation reaction is exothermic. The ice bath is taken away and stirring is continued for about 1 hour at room temperature. After the addition of 20 ml of water and 20 ml of ethyl acetate, followed by separation, the organic phase is washed with 10 ml of a saturated aqueous solution of NaCl, then dried over $MgSO_4$ and evaporated.

After silica gel column chromatography, the desired amide (1.6 g, 97%) is obtained as very bright orange crystals.

$^1$H NMR: 1.89 (s, 6H), 4.14 (br s, 2H), 7.48 (m, 2H), 8.26 (dd, 1H, J=1.7, 7.3 Hz).

Step 2: Preparation of N-{2-[4-(1,2-diphenylbut-1-en-1-yl)phenoxy]acetyl}-3,3-dimethyl-7-nitrobenzisoselenazoline.

To a solution of (Z)-1,2-diphenyl-1-(4-hydroxyphenyl)but-1-ene phenate (150 mg, 0.5 mmol) is added a solution of N-(chloroacetyl)-3,3-dimethyl-7-nitrobenzisoselenazoline (111 mg, 0.33 mmol) in THF and tetra-n-butylammonium iodide (92 mg, 0.25 mmol). The reaction mixture is heated under reflux for 1 hour, then treated following the operatory conditions described in step 3 of Example 7.

The desired amide is obtained with a yield of 95% (188 mg) as orange crystals, after silica gel column chromatography (eluent: ethyl acetate:cyclohexane, 1:10 then 1:5).

MS (EI): 598 (100), 313 (39), 207 (22), 129 (27). $^1$H NMR: 0.82 (t, 3H, J=7.5 Hz), 1.84 (s, 6H), 2.46 (q, 2H, J=7.5 Hz), 4.60 (br s, 2H), 6.62 (d, 2H, J=8.9 Hz), 6.73 (d, 2H, J=8.9 Hz), 7.0–7.55 (m, 12H), 8.25 (d, 1H, J=8.0 Hz).

Example 10

N-{8-[4-(1,2-diphenylbut-1-en-1-yl)phenoxy]octanoyl}-3,3-dimethyl-7-nitrobenzisoselenazoline Step 1: Preparation of N-(8-Bromooctanoyl)-3,3-dimethyl-7-nitrobenzisoselenazoline.

The method is identical to that used in step 1 of Example 9. The desired amide is obtained, after silica gel column chromatography (eluent: ethyl acetate:cyclohexane, 1:9 then 1:5) with a yield of 95% as bright orange crystals.

$^1$H NMR: 1.38–1.91 (m, 10H), 2.3–2.6 (br m, 2H), 3.39 (t, 2H, J=13.6 Hz), 7.38 (m, 2H), 8.21 (dd, 1H, J=1.1, 9.2 Hz).

8-bromooctanoyl chloride was prepared by heating 1 equivalent of the corresponding acid under reflux of benzene in the presence of sulfonyl chloride (2 equivalents) for 15 hours. After evaporation of the solvents followed by a second drying under a reduced pressure of 0.01 mbar, the acid chloride is used without further purification; it is a colourless liquid.

Step 2: N-{8-[4-(1,2-diphenylbut-1-en-1-yl)phenoxy]octanoyl}-3,3-dimethyl-7-nitrobenzisoselenazoline.

A solution of (Z)-1,2-diphenyl-1-(4-hydroxyphenyl)but-1-ene phenate (100 mg, 0.32 mmol) in 2 ml of THF, at room temperature, is added a solution of N-(8-bromooctanoyl)-3,3-dimethyl-7-nitrobenzisoselenazoline(100 mg, 0.22 mmol) in 2 ml of THF then tetra-n-butylammonium iodide (80 mg, 0.22 mmol).

The resulting solution is held under reflux for 2 hours.

After the usual operations of treatment of the reaction medium described in the step 3 of Example 7, the desired derivative is obtained after silica gel column chromatography (eluent: ethyl acetate:cyclohexane, 1:9 then 1:5), as orange crystals (140 mg, 93%).

MS (EI): 682 (100), 665 (22), 423 (38), 300 (45), 243 (47). $^1$H NMR: 0.92 (t, 3H, J=7.7 Hz), 1.4–1.9 (m, 12H), 1.43 (s, 6H), 2.46 (q, 2H, J=7.7 Hz), 3.81 (t, 2H, J=13.1 Hz), 6.51 (d, 2H, J=8.3 Hz), 6.78 (d, 2H, J=8.3 Hz), 7.10–7.50 (m, 12H), 8.23 (d, 1H, J=7.3 Hz).

Example 11

N-ethyl-3,3-dimethyl-7-nitrobenzisoselenazoline

According to the general protocol for the alkylation of the selenazoline described in step 1 of Example 7, the N-ethyl-3,3-dimethyl-7-nitrobenzisoselenazoline is obtained, after silica gel chromatography (eluent: ethyl acetate:cyclohexane, 1:9), with a yield of 56%, as a brown solid.

MS (EI): 286 (15), 271 (100), 115 (19). $^1$H NMR: 1.16 (t, 3H, J=7.0 Hz), 1.54 (s, 6H), 2.85 (q, 2H, J=7.0 Hz), 7.28 (dd, 1H, J=1.8, 7.3 Hz), 7.34 (t, 1H, J=7.3 Hz), 8.14 (dd, 1H, J=1.8, 7.3 Hz).

EXAMPLES OF APPLICATIONS

The operating protocols described hereafter are some non limiting examples of the implementation of the tests of activity of the compounds of the invention.

Example 12
MEASUREMENT OF THE GLUTATHIONE OXIDASE ACTIVITY OF COMPOUNDS OF GENERAL FORMULA IA To 1.5 ml of 50 mM HEPES buffer, pH 7.3, containing 2.47 mM of reduced glutathione (GSH), 0.32 mM of nicotinamide adenine dinucleotide phosphate (NADPH), and 1.23 units/ml of glutathione disulfide reductase (GR), at 37° C., are added, in the following order:

320 µl of 50 mM HEPES buffer, pH 7.3, containing 0.1 mM of DTPA, pre-equilibrated at 37° C.

30 µl of a 5 mM ethanolic mother-solution of the compound under test or 30 µl of absolute ethanol (blank). Each compound is tested at a final concentration of 81 µM.

The final reaction volume is 1850 µl.

The glutathione oxidase activity is assayed at 37° C. by measuring the reduction in absorbance at 340 nm over 5 minutes. The said initial enzymatic rate or activity is proportional to the slope of the plot of absorbance against time.

The catalytic activity for oxygen reduction in the compounds under test corresponds to the rate of consumption of NADPH. When this rate is significantly greater than that of the control, the corresponding glutathione oxidase activity can be verified directly by the measurement of the kinetics of the consumption of dissolved oxygen with the aid of a Clark electrode.

The results for the glutathione oxidase activity obtained are shown in Table 1.

After examining these results, it is noted that the compounds of general formula IA described in the present invention catalyse the oxidation of NADPH in the presence of glutathione (GSH) and glutathione disulfide reductase.

Furthermore, the effects of superoxide dismutase (SOD), catalase, iodoacetamide (IAA) and Se-GPx on the glutathione oxidase activity of the tested compounds have been studied.

To 1.5 ml of HEPES buffer, pH 7.3, containing reduced glutathione (GSH), 2.51 mM of nicotinamide adenine dinucleotide phosphate (NADPH) and 1.23 units/ml of glutathione disulfide reductase GR, at 37° C., are added in the following order:

the necessary and sufficient quantity, variable according to the case, of 50 mM HEPES, pH 7.3, containing 0.1 mM of DTPA, pre-equilibrated at 37° C.; the final reaction volume being 1850 µl.

then:
either 100 µl of a solution of 1850 units/ml of SOD in water of ultrapure quality, or 100 µl of a solution of 1850 units/ml of catalase in water of ultrapure quality and 100 µl of a solution of 1850 units/ml of SOD in water of ultrapure quality, or 150 µl of a 6.2 mM solution of iodoacetamide in 50 mM HEPES buffer, pH 7.3, containing 0.1 mM DTPA, or 100 µl of a solution of 10 units/ml of glutathione peroxidase Se-GPx in 50 mM HEPES buffer, pH 7.3, containing 0.1 mM of DTPA, or 100 µl of a solution of 1850 units/ml of SOD in water of ultrapure quality, and 100 µl of a solution of 10 units/ml of glutathione peroxidase Se-GPx in 50 mM HEPES buffer, pH 7.3, containing 0.1 mM of DPTA.

and lastly the addition of:
30 µl of a 5 mM ethanolic mother-solution of the compound under test.

The glutathione oxidase activity is assayed at 37° C. by monitoring the decrease in the absorbance at 340 nm over 15 minutes. The said initial enzymatic rate or activity is proportional to the slope of the plot of absorbance against time.

The consumption of NADPH has been calculated from the slopes of the curves obtained (OD/minute):

$$n\text{moles } NADPH \text{ oxidized/minute} = \frac{d\,NADPH}{dT} \times \frac{Vt}{\varepsilon}$$

where:

Vt=total volume of the reaction=1850 µl

ε=molar extinction coefficient of NADPH=$6.22 \times 10^6$. $M^{-1}.cm^{-1}$

The results obtained are shown in Table 1. They are expressed in nmoles of NADPH oxidized per minute.

After an examination of the results, it is noted that none of the effectors tested have any effect on the GSH oxidase activity of the molecule under test, neither separately nor in combination.

TABLE 1

Effect of SOD, catalase, SeGPx and IAA on the GSH oxidase activity

|  | nmole NADPH oxidized/min | SD | N |
|---|---|---|---|
| Bxt51062 + GSH + GR-NADPH | 77.17 | ±6.5% | 4 |
| +SOD | 78.78 | ±4.9% | 4 |
| +SOD and CAT | 79.29 | ±6.6% | 3 |
| +IAA | 76.25 | ±4.3% | 2 |
| +Se-GPx | 80.61 | ±1.2% | 3 |
| +Se-GPx and SOD | 78.45 | ±1.5% | 2 |

* SD: Standard deviation
* N: Number of tests

It is thus noted that the compounds of the invention possess a significant and specific pro-oxidizing activity. From this fact, they are useful as active ingredients in pharmaceutical compositions possessing a pro-oxidizing activity and in particular for destroying cancer cells.

Example 13
MEASUREMENT OF THE REDUCING ACTIVITY BY MONO-ELECTRONIC TRANSFER.

The ability of the molecules of general formula IA in the present invention to catalyse the reduction of an oxidizing entity by monoelectronic transfer in the presence of glutathione GSH, is demonstrated by spectrophotometrically monitoring the reduction of ferric cytochrome c to ferrous cytochrome c, at pH 7.3 and at 37° C., as a function of time.

The reaction medium is made up of:
700 µl of 50 mM HEPES buffer (pH 7.3), pre-incubated at 37° C., containing 100 µM of ferric cytochrome c, 0.1 mM of DTPA, 10 µg/ml of SOD and 110 U/ml of catalase.

the necessary and sufficient quantity, variable according to the case, of 50 mM HEPES buffer, pH 7.3, containing 0.1 mM of DTPA, pre-equilibrated at 37° C., the final reaction volume being 1 ml.

then:
either 100 µl of a solution containing 2.6 mM of NADPH and 10 units/ml of glutathione disulfide reductase in 50 mM HEPES buffer, pH 7.3, containing 0.1 mM of DTPA.

or 100 µl of a 100µM ethanolic solution of the compound under test, or 100 µl of a 10 mM glutathione GSH solution in 50 mM HEPES buffer, pH 7.3, containing 0.1 mM of DTPA.

or 100 µl of a 100µM ethanolic solution of compound under test and 100 µl of a 10 mM solution of glutathione GSH in 5 mM HEPES buffer, pH 7.3, containing 0.1 mM of DTPA.

or 100 µl of a 100 µM ethanolic solution of the compound under test and 100µl of a solution containing 2.6 mM of NADPH and 10 units/ml of glutathione disulfide reductase in 50 mM HEPES buffer, pH 7.3, containing 0.1 mM of DTPA.

or 100 µl of a 100 µM ethanolic solution of the compound under test and 100 µl of a solution containing 2.6 mM of NADPH and 10 units/ml of glutathione disulfide reductase in 50 mM HEPES buffer, pH 7.3, containing 0.1 mM of DTPA and 100 µl of a 10 mM solution of glutathione GSH in 50 mM HEPES buffer, pH 7.3, containing 0.1 mM of DTPA.

In every case, the last addition is that of the solution of the compound under test.

The increase in absorbance at 550 nm is then measured over 15 minutes, at 37° C.

Figure 1:
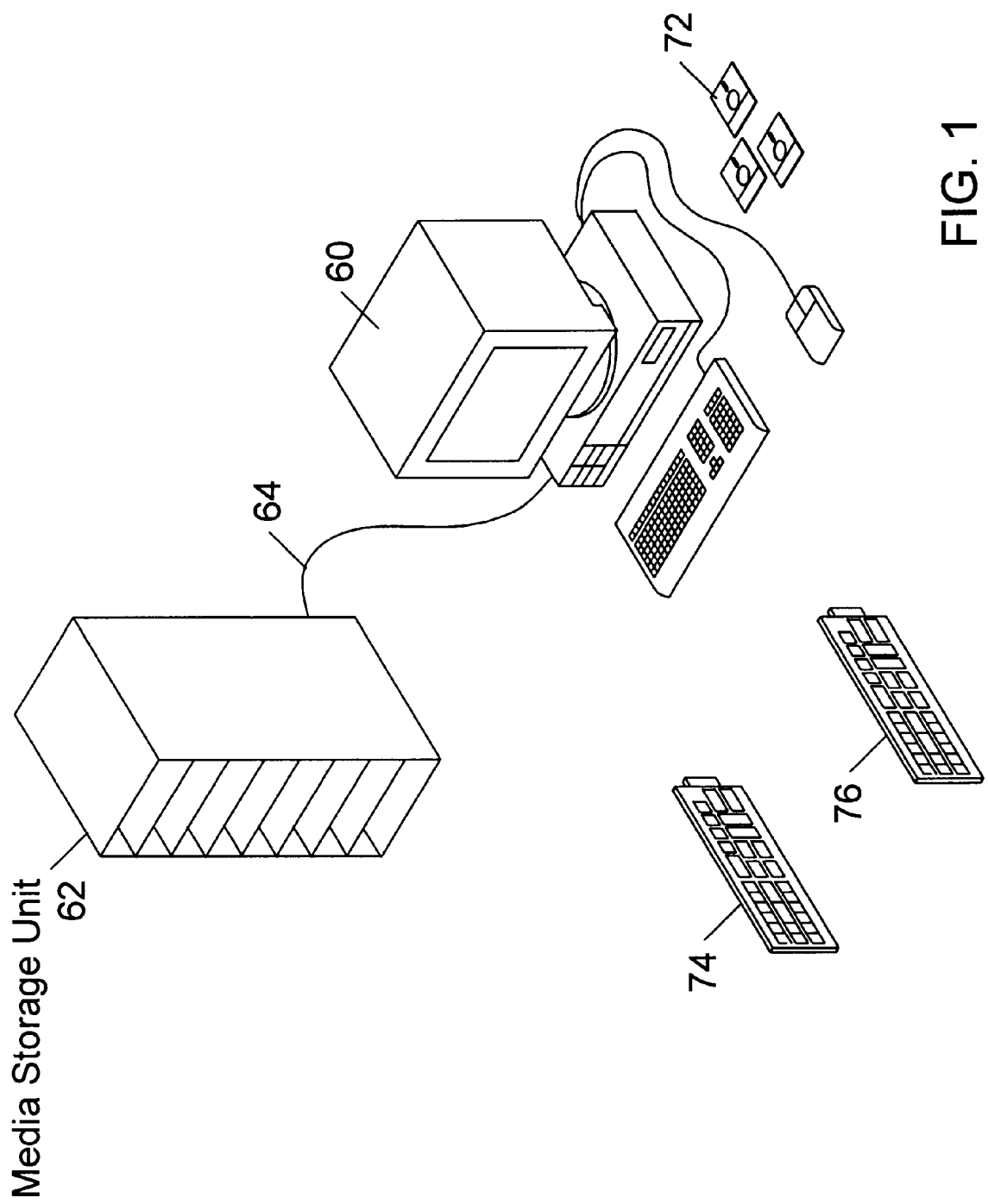
FIG. 1 represents a curve obtained in a test which demonstrates the prooxidizing activity of the compound of Example 1, namely 3,3-dimethyl-7-nitrobenzisoselenazoline, characterized by the consumption of the cofactor NADPH as a function of time, expressed in minutes, along the abcissa, and by the measured optical density, expressed in arbitrary units measured at 340 nm, on the ordinate. The curve starts at an optical density (O.D.) of 1.5 arbitrary units at time equal to 0 minutes. The control values are the values obtained in the absence of the compound of Example 1.
Figure 2:
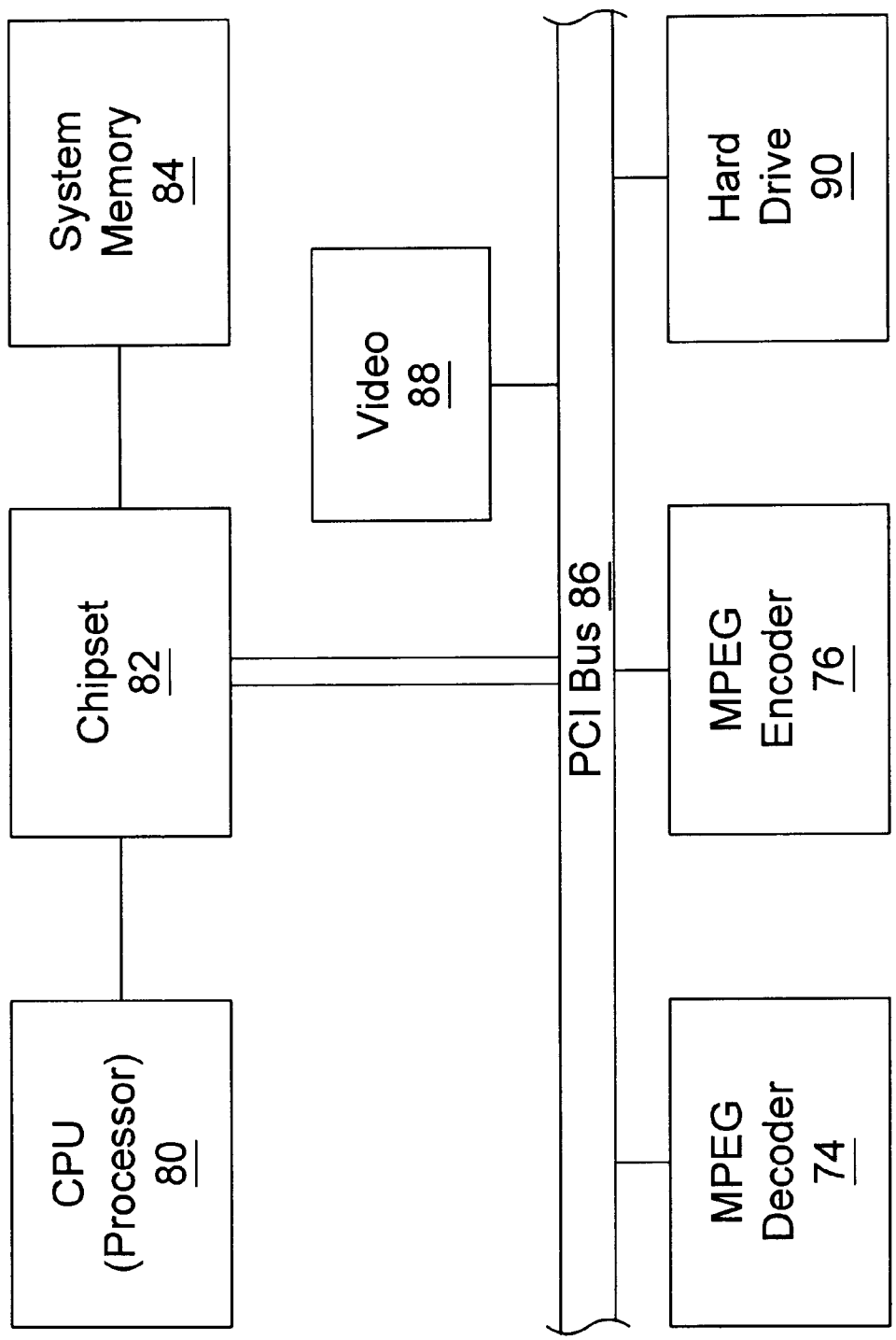
FIG. 2 represents the curve of reduction of ferric cytochrome C by a compound of the invention of Example 1, in the presence of various effectors. The concentration of ferric Cytochrome C is expressed on the ordinate in micromoles per litre ($10^{-6}$M), as a function of time, expressed in minutes, along the abcissa.

The rate of formation of reduced (ferrous) cytochrome C is proportional to the slope of the plot of absorbance against time. The kinetics of reduced cytochrome C formation is given, with the proviso that the extinction coefficient is $2.1 \times 10^{-4}$ $M^{-1}.cm^{-1}$ at 550 nm, in FIG. 2.

The results obtained demonstrate that the compounds of general structure IA described in the present invention catalyse the one-electron reduction of molecules which belong to redox couples whose reducing potential is thermodynamically greater than or equal to that of cytochrome C, in the presence of glutathione GSH and glutathione disulfide reductase. Given that these compounds, taken separately, do not reduce ferric cytochrome c, this means that the presence of glutathione GSH at the same time as glutathione disulfide reductase is required for the reducing activity of these compounds.

These results further confirm that the compounds of the invention possess a significant pro-oxidizing activity, and from this fact, they are useful as active ingredients in pharmaceutical compositions possessing a pro-oxidizing activity and in particular for destroying cancerous cells.

Example 14
CYTOTOXICITY OF COMPOUNDS OF GENERAL STRUCTURE IA ON HL60 CELLS.

Human leukemia cells HL60 are cultivated at 37° C. in 6-hole plates or in Petri dishes (diameter 35 mm) in an atmosphere of a gaseous mixture of 95% air and 5% $CO_2$, saturated with water.

The culture medium is constituted by RPMI 1640 medium, pH 7.4, containing 20% of foetal calf serum (FCS), 10 mM HEPES, 1 mM pyruvate, 4 mM of L-glutamine, 100 U/ml of penicillin and 100 μg/ml of streptomycin. Before use, the cells are centrifuged at 1500 rpm for 10 minutes at room temperature. The cellular pellet is resuspended in the RPMI-20% FCS medium in order to obtain a density of $7.10^5$ cells/ml.

The compounds of general structure IA described in the present invention are solubilised at 20 mM in absolute ethanol and diluted in the RPMI-20% FCS culture medium. The final percentage of ethanol in the reaction medium is 0.8% (v/v). The molecules are studied at the following concentrations: 80; 40; 20; 10; 5.2; 1.25; 0.62 and 0.31 μM. Two controls are carried out, in the presence and in the absence of ethanol respectively, using 100 μl of cell suspension at $7.10^5$ cells/ml incubated with 100 μl of RPMI-20% FCS medium ±0.8% of ethanol (v/v). 100 μl of an ethanolic solution of the compound under test are added to 100 μl of the suspension of HL60 cells at $7.10^5$ cells/ml and the reaction medium thus constituted is incubated for either 24 or 48 hours at 37° C., in the same culture conditions as those described above. From these incubations, the viability of the cells is measured using 3-(4,5-dimethylthiazol-2-yl)-2,5-diphenyltetrazolium bromide or MTT. MTT is metabolised by mitochondrial dehydrogenases into an insoluble dye which is therefore exclusively visualised in living cells.

MTT Test: To 200 μl of cellular suspension, obtained above, are added 50 μl of a solution of 5 mg/ml of MTT in PBS buffer. After 4 hours of incubation at 37° C., the medium is centrifuged for 10 minutes at 3000 rpm. The supernatant is removed, and 100 μl of DMSO is added to the cell pellet. This suspension is left to incubate for 10 minutes with stirring at 37° C. The developed color is measured at 550 nm against DMSO. The optical density OD=f(living cells) can then be plotted as a function of time.

The results are shown in FIGS. 3 and 4.

These results demonstrate that the compounds of general formula IA described in the present invention are taken up by the HL60 tumor cells and kill such cells at micromolar concentrations.

Example 15
CYTOTOXICITY OF COMPOUNDS OF GENERAL STRUCTURE IA ON MCF-7 CELLS.

The MCF-7 cells from a breast cancer of human origin are cultivated, in an atmosphere of a gaseous mixture of 95% air and 5% $CO_2$, saturated with water, two days before the test, in order to be in a growth phase during the toxicity test. The cells are trypsinized and are collected in a RPMI 1640 medium containing 10% FCS, 10 mM HEPES, 1 mM pyruvate, 4 mM L-glutamine, 100 U/ml penicillin, 100 μg/ml streptomycin, in order to be centrifuged at 1,500 rpm for 10 minutes. The cell pellet is resuspended in the same medium in order to obtain a cell density of 30,000 cells/cm².

The compounds of general structure IA described in the present invention are solubilised at 10 mM in absolute ethanol and diluted in RPMI-10% FCS culture medium, the final volume of ethanol in the reaction medium is 0.5% (v/v). The molecules are studied at the following concentrations: 50; 25; 12.5; 6.25; 3.125; 1.562; 0.781; 0.391 and 0.195 μM. Two controls are carried out, in the presence and in the absence of ethanol respectively, using 100 μl of cell suspension of 30,000 cells/cm² incubated with 100 μl of RPMI-10% FCS medium and ±0.5% of ethanol (v/v).

Before starting the study, the cells are rinsed with PBS buffer which contains neither calcium nor magnesium. The cells are then incubated with 200 μl of compound under test, or with the medium containing or not 0.5% of ethanol (controls) for either 24 or 48 hours under an atmosphere of a gaseous mixture of 95% air and 5% $CO_2$, saturated with water, at 37° C., then submitted to the viability test with MTT according to the following protocol.

To 200 μl of culture medium are added 50 μl of MTT at 5 mg/ml in PBS buffer. After 4 hours of incubation at 37° C., the plate is centrifuged for 10 minutes at 3,000 rpm. The supernatant is removed and the cell pellet is resuspended in 100 μl of DMSO. This is left to incubate for 10 minutes with stirring at 37° C. The coloration developed is measured at 550 nm against DMSO. The optical density OD=f(living cells) can then be plotted as a function of time.

The results are shown in FIGS. 5, 6, 7 and 8 as well as in Table 2.

The examination of the results demonstrate that the compounds of the invention are taken up by the MCF-7 tumor cells and kill such cells at micromolar concentrations.

TABLE 2

| | % OF MORTALITY OF THE MCF-7 CELLS | | | | | | | |
|---|---|---|---|---|---|---|---|---|
| | Bxt-51062 | | Bxt-57001 | | Bxt-57007 | | Bxt-57004 | |
| μm | 24 h | 48 h | 24 h | 48 h | 24 h | 48 h | 24 h | 48 h |
| 50 | 100 | 100 | 99.78 | 100 | 40.78 | 46.33 | 100 | 100 |
| 25 | 100 | 100 | 99.07 | 99.82 | 36.62 | 46.77 | 92.8 | 88.41 |
| 12.5 | 100 | 100 | 75.267 | 58.51 | 28.62 | 44.63 | 79.84 | 75.79 |
| 6.25 | 100 | 100 | 54.98 | 41.24 | 19.36 | 33.22 | 73.31 | 76.42 |
| 3.125 | 70.11 | 82.97 | 23.93 | 23.26 | 13.32 | 18.72 | 71.17 | 69.08 |
| 1.562 | 42.71 | 58.51 | 29.45 | 20 | 12.95 | 25.1 | 59.35 | 60.45 |
| 0.781 | 23.58 | 32.51 | 16.86 | 0 | 8.39 | 14.2 | 34.91 | 38.64 |
| 0.391 | 0 | 0 | 0 | 0 | 1.02 | 8.42 | 3.19 | 12.77 |
| 0.195 | 0 | 2.22 | 0 | 0 | 0 | 1.07 | 0 | 17.42 |

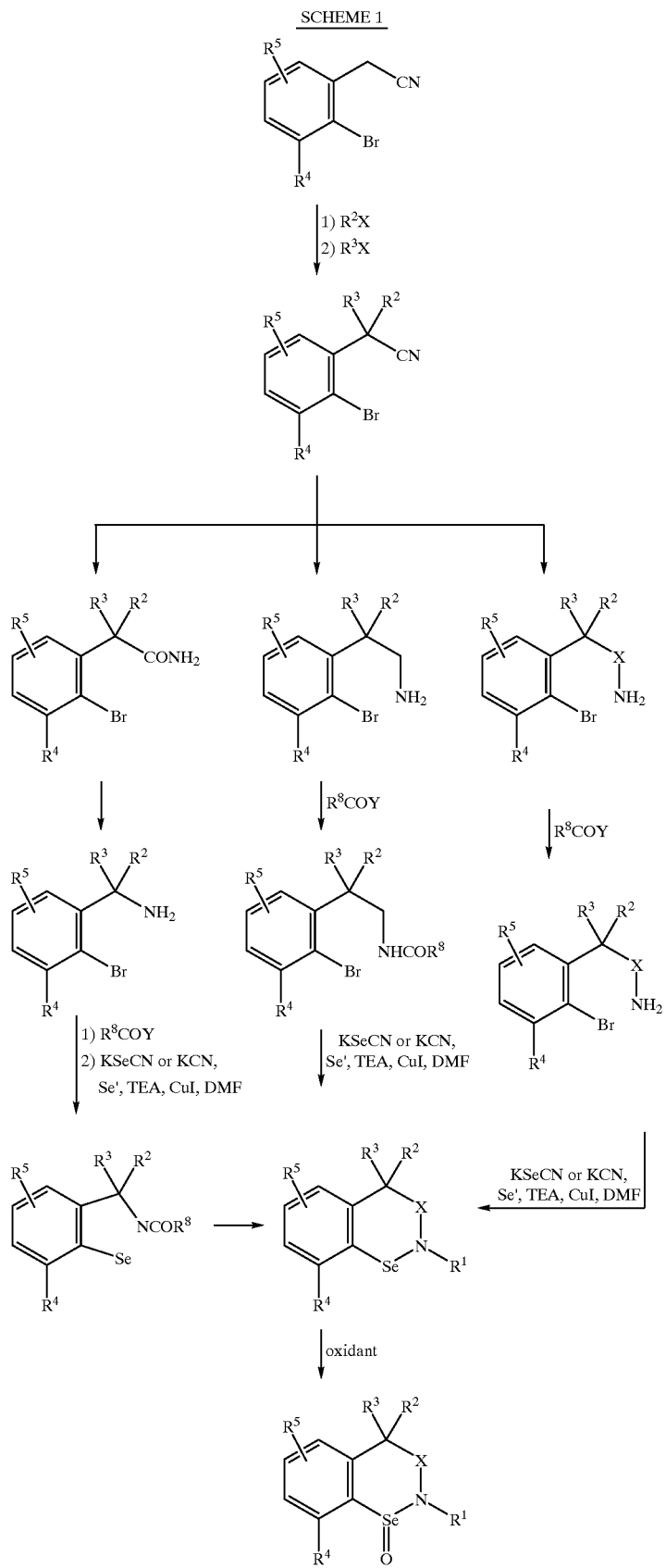
SCHEME 1

| Ex. | Structures | Ex. | Structures |
|---|---|---|---|
| 1 | BTX51062 | 7 | BTX57007 |
| 4 | BTX57004 | 8 | BXT57008 |
| 3 | BTX57005 | 9 | BXT57009 |
| 2 | BTX57006 | 10 | BXT57010 |

-continued

| Ex. | Structures | Ex. | Structures |
|---|---|---|---|
| 7 Step 1 | BTX57001 | 5 | BTX57011 |
| 11 | BTX57003 | 6 | BTX57012 |

What is claimed is:

1. A organoselenium compound of formula (I):

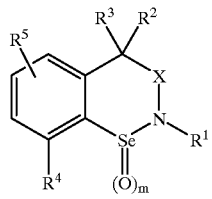

Formula I wherein:

$R^1$ is selected from a group consisting of: hydrogen; $C_1$–$C_6$ alkyl; ar($C_1$–$C_6$)alkyl; ar($C_1$–$C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; —$COR^8$; —$COOR^8$; —$CONH_2$; —$CONR^8R^9$; —$(CH_2)_pR^{10}$; and —$(CH_2)_p$Vect;

$R^2$ is selected from the group consisting of: hydrogen; $C_1$–$C_6$ alkyl; ar($C_1$–$C_6$)alkyl; ar($C_1$–$C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; —$COR^8$; —$COOR^8$; —$CONH_2$; —$CONR^8R^9$; —$(CH_2)_pR^{10}$; and —$(CH_2)_p$Vect;

$R^3$ is selected from the group consisting of: hydrogen; $C_1$–$C_6$ alkyl; ar($C_1$–$C_6$)alkyl; ar($C_1$–$C_6$)alkyl substituted on aryl by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; aryl; aryl sustituted by one or more identical or different groups selected from $C_1$–$C_6$ alkyl, trifluoromethyl, $C_1$–$C_6$ alkoxy, hydroxyl, nitro, amino, $C_1$–$C_6$ alkylamino, di($C_1$–$C_6$-alkyl)amino, sulfonyl, sulfonamide, sulfo($C_1$–$C_6$-alkyl), —$CO_2H$, and —$CO_2$—($C_1$–$C_6$)alkyl; —$COR^8$; —$COOR^8$; —$CONH_2$; —$CONR^8R^9$; —$(CH_2)_pR^{10}$; and —$(CH_2)_p$Vect;

$R^4$ is selected from the group consisting of: —$NO_2$; —NO; —CN; —$COOR^9$; —$SO_3R^9$; —$CONR^9R^{11}$ and —$SO_2NR^9R^{11}$;

$R^5$ is selected from the group consisting of: hydrogen; $C_1$–$C_6$ alkyl; —$COR^8$; —$COOR^8$; —$CONR^8R^9$; —$(CH_2)_pR^{10}$; —$(CH_2)_p$Vect; —$N^+R^{11}_3Y^-$; —$SO_3^-Z^+$ and —$CO_2^-Z^+$;

X is selected from the group consisting of: $(CR^6R^7)_n$; and CO;

R⁶ is selected from the group consisting of: hydrogen; $C_1-C_6$ alkyl; —COR⁸; —COOR⁸; —CONR⁸R⁹; —(CH₂)$_p$R¹⁰; and —(CH₂)$_p$Vect;

R⁷ is selected from the group consisting of: hydrogen; $C_1-C_6$ alkyl; —COR⁸; —COOR⁸; —CONR⁸R⁹; —(CH₂)$_p$R¹⁰; and —(CH₂)$_p$Vect;

R⁸ is selected from the group consisting of: $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —CO₂H, and —CO₂—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —CO₂H, and —CO₂—($C_1-C_6$)alkyl; heteroaryl; heteroaryl substituted by one or more identical or different groups selected from: $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —CO₂H, and —CO₂—($C_1-C_6$)alkyl; and —(CH₂)$_p$Vect;

R⁹ is selected from the group consisting of: hydrogen; $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —CO₂H, and —CO₂—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —CO₂H, and —CO₂—($C_1-C_6$)alkyl; and —(CH₂)$_p$Vect;

R¹⁰ is selected from the group consisting of: hydrogen; —N⁺R¹¹₃Y⁻; —SO₃⁻Z⁺ and —CO₂⁻Z⁺;

R¹¹ is selected from the group consisting of: hydrogen; $C_1-C_6$ alkyl; ar($C_1-C_6$)alkyl; ar($C_1-C_6$)alkyl substituted on aryl by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —CO₂H, and —CO₂—($C_1-C_6$)alkyl; aryl; aryl sustituted by one or more identical or different groups selected from $C_1-C_6$ alkyl, trifluoromethyl, $C_1-C_6$ alkoxy, hydroxyl, nitro, amino, $C_1-C_6$ alkylamino, di($C_1-C_6$-alkyl)amino, sulfonyl, sulfonamide, sulfo($C_1-C_6$-alkyl), —CO₂H, and —CO₂—($C_1-C_6$)alkyl;

Vect=

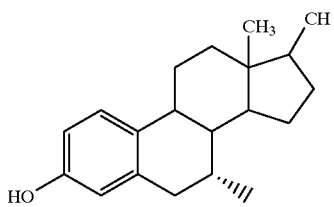

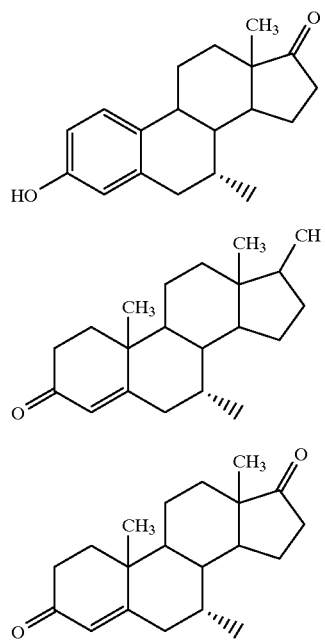

Y⁻ is the anion of a pharmaceutically acceptable acid;

Z⁺ represents the cation of a pharmaceutically acceptable base;

n=0 or 1;

m=0 or 1;

p=2 to 10;

and their pharmaceutically acceptable salts of acids or bases;

with the proviso that only one among R¹ to R³, R⁵ to R⁹ is compulsorily one Vect substituent within each molecule of the general formula I.

2. A method of treatment selected from a treatment of leukemia and a treatment of breast cancer, comprising administering to a human in need thereof an effective amount of a compound of formula I as defined in claim 1.

3. The method of claim 2, wherein the organoselenium compound of the formula (I) is included in a pharmaceutical composition in an amount ranging from 0.01 to 5% by weight, advantageously in the range 0.1 to 1% by weight, with respect to the total weight of the final composition.

4. The method according to claim 2, wherein the organoselenium compound of the formula I is included in a pharmaceutical composition in the form of unit dose in an amount ranging from 1 to 500 mg, optionally in a pharmaceutically acceptable excipient, vehicle or carrier.

5. An organoselenium compound selected from the group consisting of:

N-{8-[3,17β-dihydroxyestra-1,3,5(1 0)-trien-7α-yl]octyl}-3,3-dimethyl-7-nitrobenzisoselenazoline of formula:

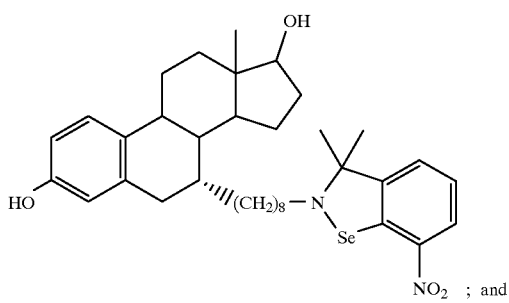

N-{8-[3,17β-dihydroxyestra-1,3,5(10)-trien-7α-yl]octanoyl}-3,3-dimethyl-7-nitrobenzisoselenazoline of formula:

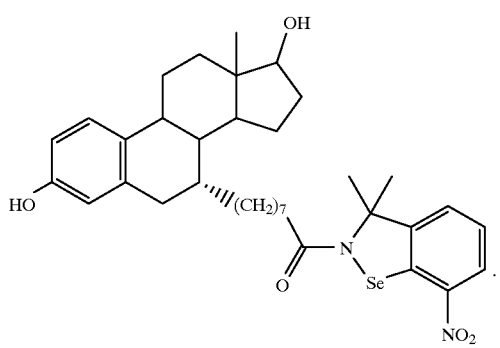

6. A pharmaceutical composition comprising, as pharmaceutically active compound:

N-{8-[3,17β-dihydroxyestra-1,3,5(10)-trien-7α-yl]octyl}-3,3-dimethyl-7-nitrobenzisoselenazoline of formula:

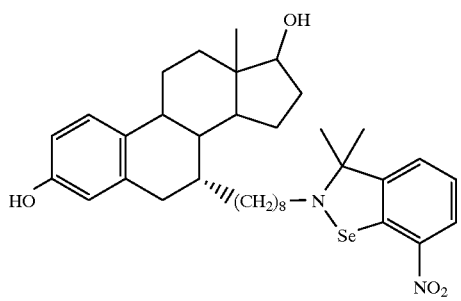

in a pharmaceutically acceptable excipient.

7. A pharmaceutically composition comprising, as pharmaceutically active compound, N-{8-[3,17β-dihydroxyestra-1,3,5(10)-trien-7α-yl]octanoyl}-3,3-dimethyl-7-nitrobenzisoselenazoline

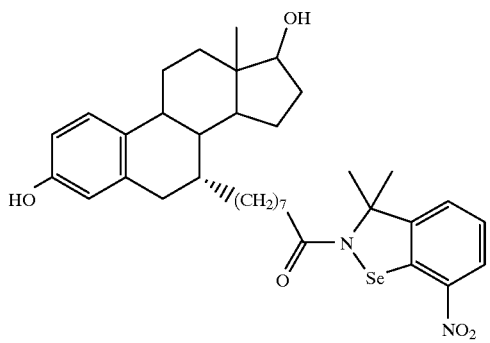

in a pharmaceutically acceptable excipient.

8. A method of treatment of leukemia, comprising administering to a human in need thereof an effective amount of N-{8-[3,17β-dihydroxyestra-1,3,5(10)-trien-7α-yl]octyl}-3,3-dimethyl-7-nitrobenzisoselenazoline of formula

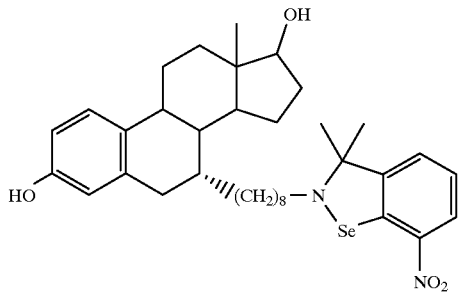

optionally in a pharmaceutically acceptable excipient.

9. A method of treatment of leukemia, comprising administering to a human in need thereof an effective amount of N-{8-[3,17β-dihydroxyestra-1,3,5(10)-trien-7α-yl]octanoyl}-3,3-dimethyl-7-nitrobenzisoselenazoline

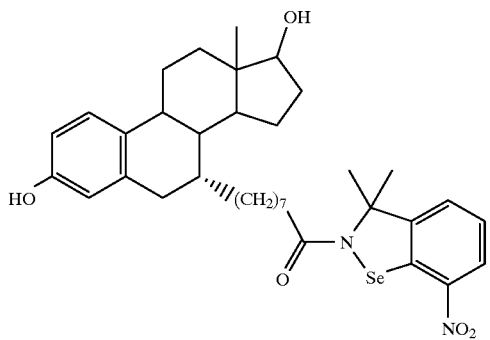

optionally in a pharmaceutically acceptable excipient.

10. A method of treatment of breast cancer, comprising administering to a human in need thereof an effective amount of N-{8-[3,17β-dihydroxyestra-1,3,5(10)-trien-7α-yl]octyl}-3,3-dimethyl-7-nitrobenzisoselenazoline of formula:

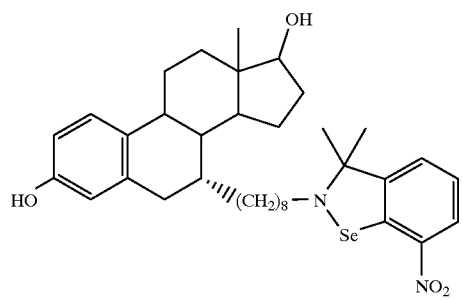

optionally in a pharmaceutically acceptable excipient.

11. A method of treatment of breast cancer, comprising administering to a human in need thereof an effective amount of N-{8-[3,17β-dihydroxyestra-1,3,5(10)-trien-7α-yl]octanoyl}-3,3-dimethyl-7-nitrobenzisoselenazoline

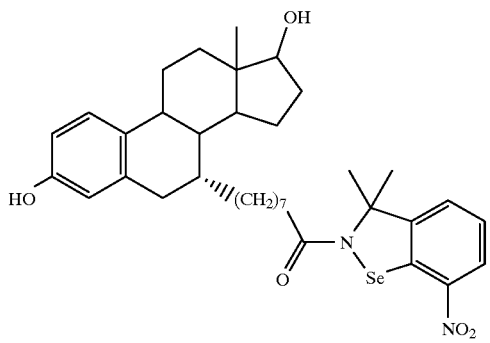

optionally in a pharmaceutically acceptable excipient.

12. A pharmaceutical composition comprising a compound of formula I in claim 1 together with a pharmaceutically acceptable carrier.

* * * * *

UNITED STATES PATENT AND TRADEMARK OFFICE
CERTIFICATE OF CORRECTION

PATENT NO. : 6,001,825
DATED : December 14, 1999
INVENTOR(S) : Jinzhu Xu, et al.

It is certified that error appears in the above-identified patent and that said Letters Patent is hereby corrected as shown below:

<u>Title page,</u>
Below the Abstract, "12 Claims, 9 Drawing Sheets" should read -- 12 Claims, 8 Drawing Sheets --

<u>Drawings,</u>
Delete Drawing sheets 1-9 and substitute attached drawing sheets 1-8.

Signed and Sealed this

Thirteenth Day of November, 2001

*Attest:*

*Attesting Officer*

NICHOLAS P. GODICI
*Acting Director of the United States Patent and Trademark Office*